(12) United States Patent
Dannhardt et al.

(10) Patent No.: US 7,223,781 B2
(45) Date of Patent: May 29, 2007

(54) 2-MERCAPTO-4,5-DIARYLIMIDAZOLE DERIVATIVES AND THE USE THEREOF AS CYCLOOXYGENASE INHIBITORS

(75) Inventors: Gerd Dannhardt, Mainz (DE); Linda Hahn, Hattersheim (DE)

(73) Assignee: Beiersdorf AG, Hamburg (DE)

( * ) Notice: Subject to any disclaimer, the term of this patent is extended or adjusted under 35 U.S.C. 154(b) by 245 days.

(21) Appl. No.: 10/672,613

(22) Filed: Sep. 26, 2003

(65) Prior Publication Data

US 2004/0116695 A1 Jun. 17, 2004

Related U.S. Application Data

(63) Continuation of application No. PCT/EP02/03264, filed on Mar. 22, 2002.

(30) Foreign Application Priority Data

Mar. 26, 2001 (DE) ................ 101 14 775

(51) Int. Cl.
*A61K 31/4174* (2006.01)
*C07D 233/66* (2006.01)
(52) U.S. Cl. .............. 514/398; 548/343.5; 514/398
(58) Field of Classification Search ............. 548/311.1, 548/343.5; 514/398
See application file for complete search history.

(56) References Cited

U.S. PATENT DOCUMENTS

| | | | |
|---|---|---|---|
| 4,269,847 A | | 5/1981 | Niedballa et al. |
| 4,355,039 A | * | 10/1982 | Niedballa et al. ............ 514/398 |
| 4,440,776 A | | 4/1984 | Niedballa et al. |
| 4,686,231 A | | 8/1987 | Bender et al. |
| 5,318,984 A | * | 6/1994 | Billheimer et al. ......... 514/398 |
| 5,364,875 A | * | 11/1994 | Wilde ........................ 514/375 |
| 5,620,999 A | | 4/1997 | Weier et al. |

FOREIGN PATENT DOCUMENTS

| | | |
|---|---|---|
| JP | 01040467 | 2/1989 |
| RU | 1415725 A1 | 1/1996 |
| WO | WO 91/10662 | 7/1991 |
| WO | WO 91/13876 | 9/1991 |

OTHER PUBLICATIONS

STN CAS Accession No. 1973:72002, "Reactions with 4,5-disubstituted 2-mercaptoimidazoles and their derivatives," Mustafa et al, Journal fuer Praktische Chemie (1972), vol. 314, No. (5-6), pp. 785-792.*
STN CAS Accession No. 1983:470631, "Heterocyclic systems containing bridgehead nitrogen atom. Part XLVI . . . " Gupta et al. Indian Journal of Chemistry, Section B. (1983), vol. 22B, No. (3), pp. 268-269.*
Maduskuie, Thomas P., Jr., et al., "Design, Synthesis, and Structure-Activity Relationship Studies for a New Imidazole Series of J774 Macrophage Specific Acyl-CoA:Cholesterol Acyltransferase (ACAT) Inhibitors," J. Med. Chem., 1995, pp. 1067-1083, vol. 38, XP001084249, American Chemical Society, U.S.A.
Mustafa, A., et al., "Reactions with 4,5-Disubstituted 2-Mercaptoimidazoles and their Derivatives," J. Prakt. Chem., 1972, pp. 785-792, vol. 314, XP-001088374, J. A. Barth, Leipzig.
Gupta, G. D., et al., "Heterocyclic Systems Containing Bridgehead Nitrogen Atom. Part XLVI, Reaction of 4,5-disubstituted 2-mercaptoimidazoles with alpha-halogenoketones and 1,2-dibromoethane," Indian J. Chemical, Chemical Abstracts, Aug. 29, 1983, vol. 99, No. 9, Abstract No. 70631, Columbus, Ohio.
Salama, M.A., et al., "Synthesis and reactions of 4,5-diaryl-2-mercaptoimidazoles," Chemical Abstracts, Nov. 7, 1988, p. 710, vol. 109, No. 19, Abstract No. 170305, Columbus, Ohio.
Wilde, Richard G., et al., "Acyl CoA: Cholesterol Acyltransferase (ACAT) Inhibitors: Heterocyclic Bioisosteres for the Urea Group in DuP 128," Bioorganic & Medicinal Chemistry Letters, Jan. 19, 1995, pp. 177-180, vol. 5, No. 2, XP004135812, Elsevier Science Ltd., Great Britain.
International Search Report from corresponding International Application No. PCT/EP02/03264 dated Aug. 2, 2002.

* cited by examiner

*Primary Examiner*—Joseph K. McKane
*Assistant Examiner*—Janet L. Coppins
(74) *Attorney, Agent, or Firm*—Alston & Bird LLP

(57) ABSTRACT

The invention relates to the 2-mercapto-4,5-diarylimidazole derivatives of formula (I), wherein $R^1$, $R^2$, $R^3$ and $R^4$ are defined as in the description. The inventive compounds have an immunomodulatory and cyclooxygenase-inhibiting activity and are therefore suitable for the treatment of diseases that are associated with a disturbed immune system.

20 Claims, No Drawings

2-MERCAPTO-4,5-DIARYLIMIDAZOLE DERIVATIVES AND THE USE THEREOF AS CYCLOOXYGENASE INHIBITORS

CROSS-REFERENCE TO RELATED APPLICATIONS

This is a continuation application of PCT/EP02/03264, filed Mar. 22, 2002, which is incorporated herein by reference in its entirety, and also claims the benefit of German Priority Application No. 101 14 775.9, filed Mar. 26, 2001.

FIELD OF THE INVENTION

The present invention relates to 2-mercapto-4,5-diarylimidazole derivatives having immunomodulating and cyclooxygenase-inhibiting action, pharmaceutical compositions which contain the compound, and their use in pharmacy.

BACKGROUND OF THE INVENTION

The action of conventional nonsteroidal antiinflammatories, such as acetylsalicylic acid, is essentially based on the inhibition of cyclooxygenase, an enzyme of the arachidonic acid cascade, which is also known as prostaglandin G/H synthase. Meanwhile, two different forms of cyclooxygenase have been found, which are designated as COX-1 and COX-2. Despite numerous investigations, the biochemical mode of action of the two enzymes is not yet completely elucidated. Various studies have shown, however, that they play an essential role in numerous diseases and inflammatory processes.

Pharmacologically active imidazole compounds which inhibit cyclooxygenase-1 and -2 are already known. In J. Med. Chem. 1996, 39, 3927-37, for example, imidazole derivatives having 5-lipoxygenase- and cyclooxygenase-inhibiting action are described, 2-(4-methylsulfinylphenyl)-4-(4-fluorophenyl-5-(pyrid-4-yl)imidazole also having a cytokine-inhibiting action.

WO 95/00501 describes further phenylheterocycles which have a cyclooxygenase-inhibiting action, among these also 4,5-diaryl-substituted imidazoles, for the treatment of diseases which are connected with cyclooxygenase.

Pharmaceutically active imidazole derivatives are further known which contain 4,5-di-(hetero)arylimidazole elements and are substituted in the 2-position. U.S. Pat. No. 4,585,771 discloses, for example, 4,5-diphenylimidazole derivatives which are substituted in the 2-position by a pyrrolyl, indolyl, imidazolyl or thiazolyl radical and have an antiinflammatory and antiallergic activity. U.S. Pat. Nos. 4,528,298 and 4,402,960 furthermore describe 4,5-di(hetero)arylimidazole derivatives, which are substituted in the 2-position with a phenyl, pyridyl, N-oxypyridyl, pyrimidyl, thiazolyl or thienyl radical, and have an antiinflammatory and antiallergic activity.

DE 198 42 833 relates to 4-heteroaryl-5-phenylimidazole derivatives which are substituted in the 2-position by a phenylalkylthio group. These compounds act as antiinflammatories and inhibitors of cytokine release. WO 99/03837, WO 93/14081 and DE 198 42 833 describe 2-substituted imidazoles which inhibit the synthesis of a number of inflammatory cytokines. These compounds alternatively have a further substituent on the nitrogen atom in the 1-position.

Further pharmacologically active imidazole derivatives are known from U.S. Pat. Nos. 4,461,770, 4,584,310, JP 0140467, DE 28 23 197, EP 372445, WO 91/10662, Acta Chim. 1969, 61, 69-77 and J. Prakt. Chem. 1972, 314, 785-792.

It is known that the conventional nonsteroidal antiinflammatories have a number of undesired side effects, in particular gastrointestinal side effects, nephrotoxicity and allergic reactions. It was further found that the known compounds are not stable and are difficult to process or have a low activity.

In spite of the numerous known compounds, there is therefore furthermore a need for compounds having antiinflammatory, antipyretic and analgesic action, which inhibit the release of various cytokines and serve as inhibitors of the mediators of the arachidonic acid cascade. In particular there is a need for compounds which act not only on the parameters which are decisive in acute diseases, but which also can intervene in the immunological processes crucial for the chronic course (cytokine release, expression of cell-surface antigens). In particular, owing to the importance of the COX enzymes for a number of further pathological processes, e.g.: colon carcinoma, overshooting angiogenesis, excitatory neuronal processes, wound healing etc, the development of COX inhibitors has a novel and additional importance.

SUMMARY OF THE INVENTION

The object of the invention is the provision of such compounds.

Surprisingly, it has now been found that certain 2-mercapto-4,5-diarylimidazole derivatives are stable compounds which are easy to process, and which have a high cyclooxygenase-inhibiting action with a variable COX-1/COX-2 selectivity.

The present invention therefore relates to the 2-mercapto-4,5-diarylimidazole derivatives of the formula:

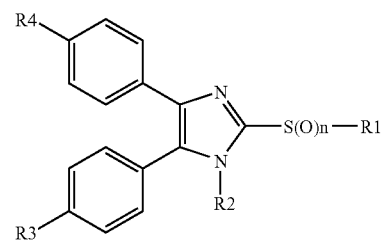

in which
R$^1$ has the following meanings:
  CONR$^5$R$^6$, in which R$^5$ and R$^6$ independently of one another are H or C$_1$-C$_6$-alkyl or, together with the nitrogen atom to which they are bonded, form a saturated heterocyclic radical having 5 or 6 ring atoms and one or two heteroatoms which independently of one another are selected from N and O;
  A-CONR$^5$R$^6$, in which A is C$_1$-C$_6$-alkylene which is optionally substituted by C$_1$-C$_3$-alkyl-CO, and R$^5$ and R$^6$ independently of one another are H, C$_1$-C$_6$-alkyl or phenyl which is optionally substituted by one or 2 halogen atoms;
  C$_1$-C$_6$-alkylene-R$^7$, where R$^7$ is NR$^5$R$^6$, an aromatic heterocyclic radical having 5 or 6 ring atoms and one or two heteroatoms, which independently of one another are selected from N, S and O, where the heterocyclic radical can optionally be fused to a benzene ring, or is COOR$^8$, R$^5$ and R$^6$ independently of one another are H or C$_1$-C$_6$-alkyl and R$^8$ is H or C$_1$-C$_6$-alkyl;

C$_1$-C$_6$-alkylene-CO—R$^9$, where R$^9$ is phenyl which is optionally substituted by halogen;

C$_1$-C$_6$-alkylene-NR$^{10}$—CO—R$^{11}$, or

C$_1$-C$_6$-alkylene-NR$^{10}$—SO$^2$—R$^{12}$,

R$^{10}$ is H or C$_1$-C$_6$-alkyl,

R$^{11}$ is phenyl which is optionally substituted by 1, 2 or 3 substituents, which independently of one another are selected from halogen, CN, NO$_2$, CF$_3$, OC$_1$-C$_6$-alkyl and C$_1$-C$_6$-alkyl, naphthyl, C$_1$-C$_6$-alkyl which is optionally substituted by 1 or 2 phenyl groups, C$_2$-C$_6$-alkenyl, CH═CH-phenyl, an aromatic, heterocyclic radical having 5 or 6 ring atoms and 1 or 2 heteroatoms, which independently of one another are selected from N, O and S, or NR$^5$R$^6$, where R$^5$ and R$^6$ independently of one another are H or C$_1$-C$_6$-alkyl;

R$^{12}$ is phenyl which optionally has 1, 2 or 3 substituents which independently of one another are selected from halogen, NO$_2$, CF$_3$, OC$_1$-C$_6$-alkyl, C$_1$-C$_6$-alkyl, NH$_2$ and NHCOC$_1$-C$_3$-alkyl, C$_1$-C$_6$-alkyl which is optionally substituted by one or two phenyl groups, or naphthyl, R$^2$ is H, C$_1$-C$_6$-alkyl or (CH$_2$)$_o$COOH, R$^3$ and R$^4$, which can be identical or different, are H, OH, OC$_1$-C$_6$-alkyl, halogen or C$_1$-C$_6$-alkyl which is substituted by 1, 2 or 3 halogen atoms, n is 0, 1 or 2 and o is 0, 1, 2, 3 or 4, and the optical isomers and physiologically tolerable salts thereof.

If the compounds according to the invention contain asymmetric centers, racemates and optical isomers (enantiomers, diastereomers) are included.

DETAILED DESCRIPTION OF PREFERRED EMBODIMENTS

The expression "alkyl" (also in combinations with other groups, such as aminoalkyl, alkylsulfonyl etc.) includes straight-chain and branched alkyl groups preferably having 1 to 6 and in particular 1 to 4 C atoms, such as methyl, ethyl, n- and i-propyl, n-, i- and t-butyl, sec-butyl, n-pentyl and n-hexyl.

If alkyl is substituted by halogen, preferably 1, 2 or 3 halogen substituents are present. Preferred examples of halogen-substituted alkyl are chloromethyl, CHF$_2$ and in particular CF$_3$.

The expression "alkylene" preferably represents a straight-chain or branched alkylene group having 1 to 6, preferably 1 to 4, C atoms, such as methylene, ethylene, ethylidene, 1,2- or 1,3-propylene, 1,4-butylene or 1,6-hexylene.

The expression "alkenyl" represents a straight-chain or branched alkenyl group having 2 to 6 and in particular 2 to 4 C atoms, such as —CH═CH$_2$, —CH═CHCH$_3$ or —CH$_2$—CH═CH$_2$.

The expression "halogen" represents a fluorine, chlorine, bromine or iodine atom, in particular a fluorine or chlorine atom.

Nonaromatic heterocyclic radicals are preferably piperidinyl, pyranyl, morpholinyl or pyrrolidinyl.

Preferred aromatic heterocyclic radicals are pyridyl, in particular 2-, 3- or 4-pyridyl, furyl, in particular 2-furyl, thienyl, in particular 2-thienyl, pyrimidinyl, pyrrolyl, imidazolyl, oxazolyl, isoxazolyl or thiazolyl. Furyl and thienyl are preferred.

If R$^7$ represents a radical fused to a benzene ring, it is preferably quinolyl, in particular 2-quinolyl, or benzimidazole, in particular 2-benzimidazole.

Compounds of the formula I are preferred where one of the radicals R$^3$ and R$^4$ is an OH group or C$_1$-C$_6$-alkoxy group, preferably a methoxy group. Additionally preferably, both radicals R$^3$ and R$^4$ are an OH group or C$_1$-C$_6$-alkoxy group, preferably a methoxy group. Particularly preferably, one or both radicals R$^3$ and R$^4$ are a C$_1$-C$_6$-alkoxy group, in particular OCH$_3$.

Compounds of the formula I are furthermore preferred where R$^2$ is hydrogen or methyl, preferably hydrogen.

Preferred embodiments are as follows:

a) R$^1$ is CONR$^5$R$^6$, where R$^5$ and R$^6$ independently of one another are H or C$_1$-C$_6$-alkyl or, together with the nitrogen atom to which they are bonded, are morpholino, piperidino or pyrrolidino;

R$^2$ is H or C$_1$-C$_6$-alkyl and at least one of the radicals R$^3$ and R$^4$ is OC$_1$-C$_6$-alkyl;

b) R$^1$ is A—CONR$^5$R$^6$,

A is methylene, ethylene, ethylidene or —CH(COCH$_3$)—

R$^2$ is H or C$_1$-C$_6$-alkyl, at least one of the radicals R$^3$ and R$^4$ is OC$_1$-C$_6$-alkyl and R$^5$ and R$^6$ independently of one another are H, C$_1$-C$_6$-alkyl, phenyl or halogen-substituted phenyl, in particular chlorine-substituted phenyl.

The substituent is particularly preferably situated in the H-position.

c) R$^1$ is C$_1$-C$_6$-alkylene-R$^7$,

R$^7$ is NR$^5$R$^6$,

R$^5$ and R$^6$ independently of one another are H or C$_1$-C$_6$-alkyl,

R$^2$ is H or C$_1$-C$_6$-alkyl and at least one of the radicals R$^3$ and R$^4$ is OC$_1$-C$_6$-alkyl;

d) R$^1$ is C$_1$-C$_6$-alkylene-R$^7$,

R$^7$ is 2-pyridyl, 3-pyridyl, 4-pyridyl, quinolyl or benzymidazolyl,

R$^2$ is H or C$_1$-C$_6$-alkyl, at least one of the radicals R$^3$ and R$^4$ is OC$_1$-C$_6$-alkyl and C$_1$-C$_6$-alkylene is methylene.

e) R$^1$ is C$_1$-C$_6$-alkylene-R$^7$,

R$^7$ is an aromatic heterocyclic radical having 5 or 6 ring atoms and one or two heteroatoms which independently of one another are selected from N, S and O, R$^2$ is (CH$_2$)$_o$COOH, o is 0, 1, 2, 3 or 4, at least one of the radicals R$^3$ and R$^4$ is OC$_1$-C$_6$-alkyl.

The heterocyclic radical is preferably pyridyl.

f) $R^1$ is $C_1$-$C_6$-alkylene-CO—$R^9$,
  $R^9$ is phenyl or phenyl which is substituted by halogen, in particular chlorine, where substitution in the 4-position is particularly preferred,
  $R^2$ is H or $C_1$-$C_6$-alkyl, and
  at least one of the radicals $R^3$ and $R^4$ is $OC_1$-$C_6$-alkyl.

g) $R^1$ is $C_1$-$C_6$-alkylene-$NR^{10}$—CO—$R^{11}$,
  $R^2$ is H or $C_1$-$C_6$-alkyl,
  at least one of the radicals $R^3$ and $R^4$ is $OC_1$-$C_6$-alkyl,
  $R^{10}$ is H or $C_1$-$C_6$-alkyl,
  $R^{11}$ is phenyl which optionally has one or two substituents which independently of one another are selected from halogen, CN, $NO_2$ and $CF_3$, where the substituents are preferably situated in the 2- and/or 4-position.

$C_1$-$C_6$-alkylene is particularly preferably ethylene.

h) $R^1$ is $C_1$-$C_6$-alkylene-$NR^{10}$—CO—$R^{11}$, where $R^2$, $R^3$, $R^4$, $R^{10}$ and $C_1$-$C_6$-alkylene have the meanings indicated above under g) and $R^{11}$ is $C_1$-$C_6$-alkyl, benzyl, phenylethyl, CH=CHPh or $CH(Ph)_2$.

i) $R^1$ is $C_1$-$C_6$-alkylene-$NR^{10}$—$SO_2$—$R^{12}$, where $R^2$, $R^3$, $R^4$, $R^{10}$ and $C_1$-$C_6$-alkylene have the meanings indicated above under g) and $R^{12}$ is furyl, thienyl or naphthyl.

j) $R^1$ is $C_1$-$C_6$-alkylene-$NR^{10}$—CO—$R^{11}$, where $R^2$, $R^3$, $R^4$, $R^{10}$ and $C_1$-$C_6$-alkylene have the meanings indicated above under g) and $R^{11}$ is phenyl, which optionally has one, two or three substituents which independently of one another are selected from halogen, $NO_2$, $CF_3$, $C_1$-$C_6$-alkyl and $NHCOC_1$-$C_3$-alkyl, or $C_1$-$C_6$-alkyl, benzyl or naphthyl.

k) $R^1$ is —$CH_2$-$R^7$,
  $R^7$ is $COOR^8$,
  $R^8$ is H or $C_1$-$C_6$-alkyl,
  $R^2$ is H or $C_1$-$C_6$-alkyl and
  at least one of the radicals $R^3$ and $R^4$ is $OC_1$-$C_6$-alkyl.

Particularly preferably, in the above embodiments a) to k) both radicals $R^3$ and $R^4$ are $OC_1$-$C_6$-alkyl.

The physiologically tolerable salts can in the present case be acid addition or base addition salts. For acid addition salts, inorganic acids such as hydrochloric acid, sulfuric acid or phosphoric acid are employed or organic acids such as tartaric acid, citric acid, maleic acid, fumaric acid, malic acid, mandelic acid, ascorbic acid, gluconic acid and the like.

The compounds according to the invention are prepared in a 2-stage process. First, the synthesis of a 4,5-diaryl-1H-imidazole-2-thiol is carried out. This is then reacted in the second step such that the desired substituents are introduced. The substituents are preferably introduced into the positions 1 and 2 on the nitrogen or sulfur atom.

The preparation of the compounds according to the invention is illustrated by way of example of compounds in which $R^3$ and $R^4$ are both a methoxy group. Compounds having other radicals $R^3$ and $R^4$ can be prepared in a corresponding manner.

1) Preparation of the 4,5-diaryl-1H-imidazole-2-thiols
  a) Symmetrically substituted 4,5-diaryl-1H-imidazole-2-thiols By reacting the corresponding benzoins (compounds 1), which are obtainable by benzoin condensation, e.g., according to Houben-Weyl, Methoden der organischen Chemie (Methods of organic chemistry), volume 7/2a, Thieme-Verlag, Stuttgart, 1973, 653-671, with thiourea, symmetrically substituted 4,5-diaryl-1H-imidazole-2-thiols (compounds 2) are synthesized by the process from scheme I. The process is described in Liebigs Ann. Chem. 1895, 284, 24-29.

Scheme 1:

Synthesis of symmetrically substituted 4,5-diaryl-1H-imidazole-2-thiols

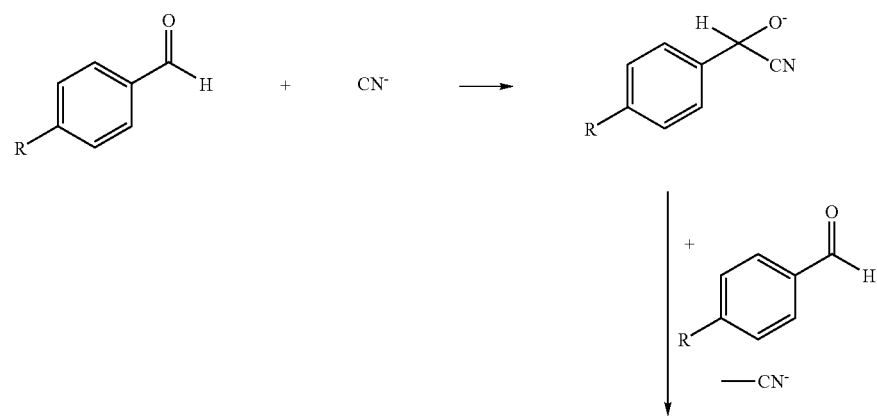

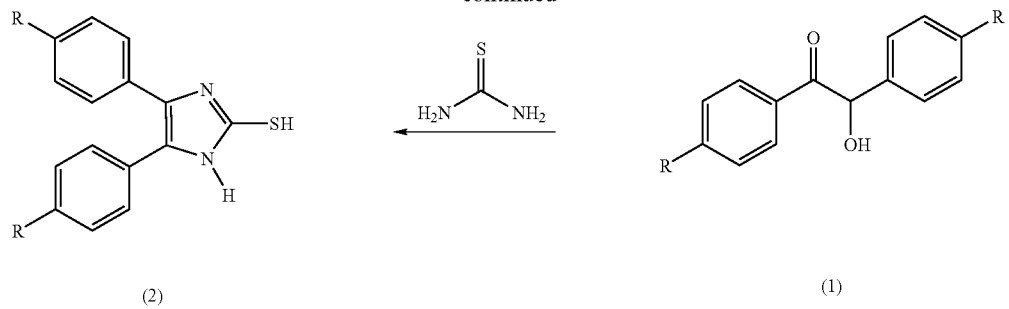

(2)  (1)

b) Unsymmetrically substituted 4,5-diaryl-1H-imidazole-2-thiols

Unsymmetrically substituted 4,5-diaryl-1H-imidazole-2-thiols are, however, preferably synthesized according to the process from scheme II. In this process, an aldehyde is reacted with 1,3-propanedithiol in the presence of an acid, the polarity of the electrophilic carbon of the carbonyl group being reversed by conversion to the cyclic dithioacetal. The methyl group between the two sulfur atoms can be deprotonated using a strong base such as n-butyllithium, which makes possible the addition of another aldehyde, see J. Org. Chem. 1966, 31, 4303-4304. The thioacetal function is then converted into the corresponding carbonyl compound by addition of a mercury salt, see Liebigs Ann. Chem. 1981, 10-19. The benzoins thus obtained are then reacted with thiourea according to the condensation already described, the unsymmetrically substituted 4,5-diaryl-1H-imidazole-2-thiols of the formula 2 in scheme 2 being formed.

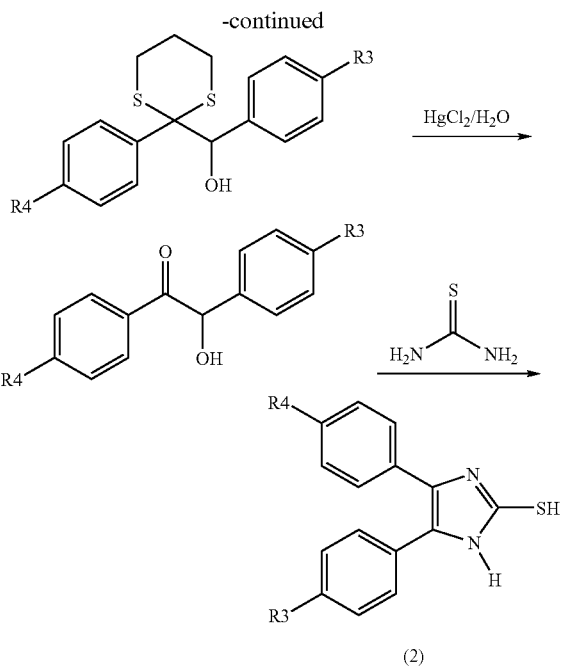

(2)

Scheme 1:

Synthesis of unsymmetrically substituted 4,5-diaryl-1H-imidazole-2-thiols

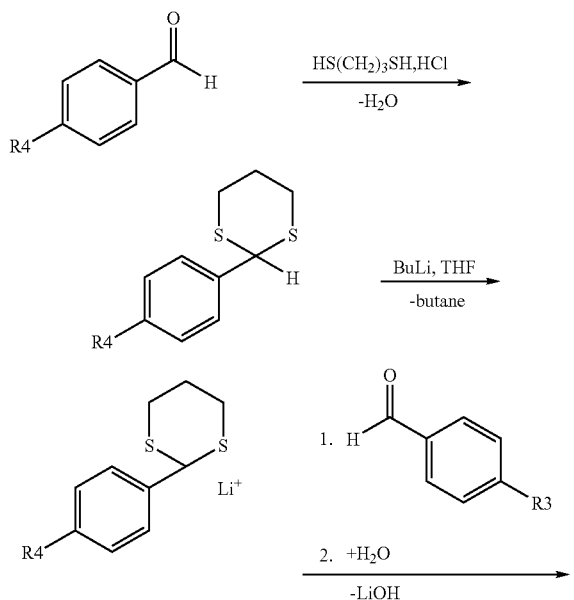

2. Introduction of the desired substituents

The substitutions of the 4,5-diaryl-1H-imidazole-2-thiols can be carried out by customary processes. These include reactions for the substitution of the sulfur in position 2 of the imidazole ring by nucleophilic substitution for the introduction of a group having an alkyl, amine, aryl ketone, acetic acid ethyl ester, carbonyl and substituted carbonyl function.

The nucleophilic substitution of the thiols is carried out by reaction with the side chain to be introduced, which has a suitable leaving group, e.g. a halogen atom, in particular a bromine or iodine atom, the methanesulfonyl or toluenesulfonyl group. The reaction is customarily carried out in the presence of a base, such as sodium carbonate or potassium carbonate or the sodium or potassium salt of the thiol is employed, which is generated by reaction of the thiol with a base, such as a sodium or potassium alkoxide. The substitution is in general carried out in a polar organic solvent, such as methanol, ethanol, dimethylformamide etc, and at a temperature in the range from room temperature up to the boiling point of the reaction mixture.

The introduction of a side chain using a carboxylic acid amide or sulfonamide group is expediently carried out according to scheme 3 below:

Scheme 3:

Synthesis of compounds of the formula I having carboxylic acid amide or sulfonamide side chains

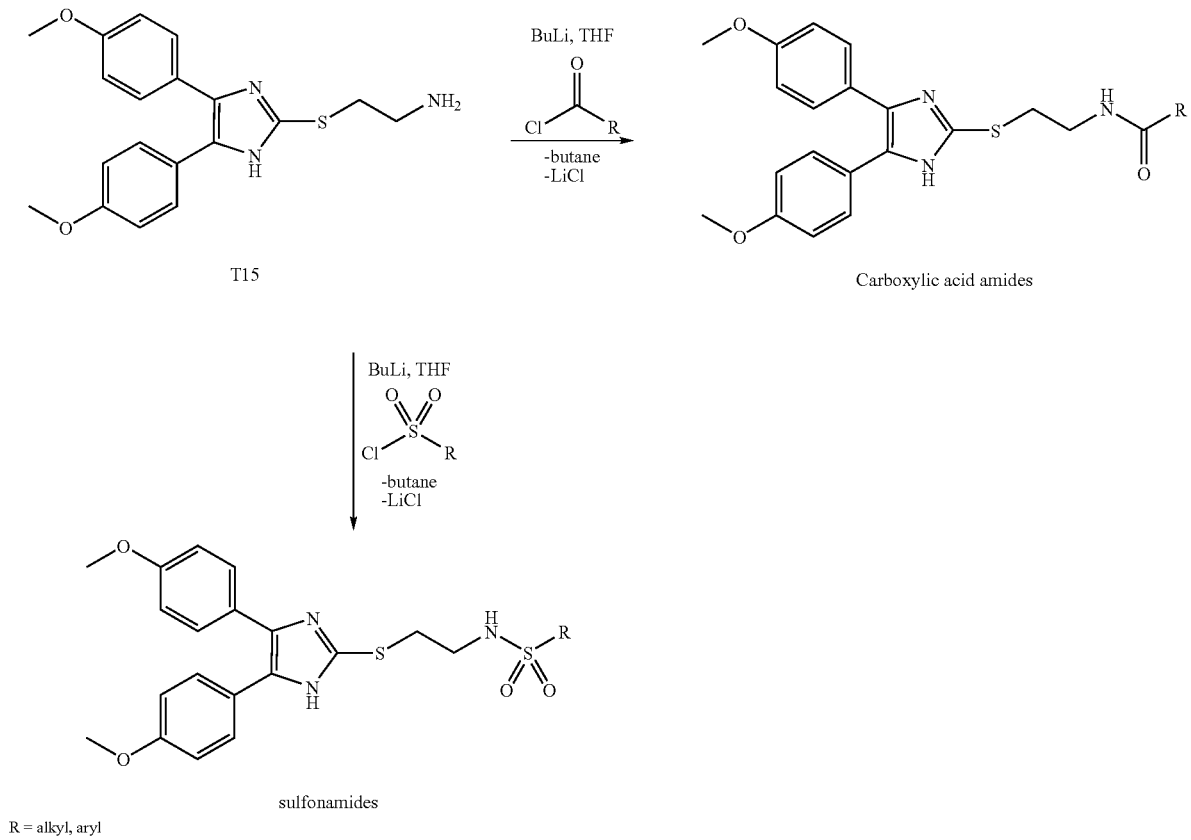

R = alkyl, aryl

The compound T15 is prepared by nucleophilic substitution as described above. The reaction of T15 is then carried out in a polar, aprotic organic solvent, such as tetrahydrofuran (THF), dioxane etc. at a temperature in the range from −60° C. to approximately ambient temperature.

The preparation of the compounds of the formula I having a urea group in the side chain is carried out in a customary manner.

The oxidation of the sulfur in the 2-position of the imidazole to the corresponding sulfinyl or sulfonyl compound is carried out according to customary processes using a suitable oxidant, e.g., m-chloroperbenzoic acid, hydrogen peroxide, benzoyl peroxide etc.

The compounds according to the invention are potent selective inhibitors of cyclooxygenase. Cyclooxygenase is an enzyme of the arachidonic acid cascade, in which prostaglandins, for example the prostaglandins $G_2$ and $H_2$, and thromboxanes are formed from the $C_{20}$-carboxylic acid arachidonic acid.

The compounds according to the invention are suitable on account of their cyclooxygenase-inhibiting action as antiallergic, antipyretic and analgesic active compounds for the treatment of diseases which are connected with a disturbance of the immune system. They are suitable, for example, for the inhibition of prematurely commencing labor, for the treatment of cancer, for example colon carcinoma, and Alzheimer's disease. Further possibilities of use are offered in the treatment of autoimmune diseases, rheumatoid arthritis, gout, septic shock, osteoporosis, neuropathic pain, alopecia, psoriasis, acute pancreatitis, rejection reactions in allogenic transplants, allergically caused pneumonia, arteriosclerosis, multiple sclerosis, cachexia and inflammatory bowel disease (IBD), adenomatous polyposis (Gardner's syndrome), and colon carcinoma, for the inhibition of angiogenesis in connection with oncoses. Moreover, the compounds are utilizable for the topical treatment of inflammations of differing origin (contact eczema, erythema, such as UV erythema).

The compounds according to the invention can be administered either as individual active compounds or as mixtures with other therapeutic active compounds. The compounds can be administered systemically or as topical active compounds. The compounds can be administered on their own, but in general they are dosed and administered in the form of pharmaceutical compositions, i.e., as mixtures of the active compounds with suitable pharmaceutical carriers or diluents. For systemic action, the compounds or compositions can be administered orally or parenterally, preferably they are given in oral dosage forms.

The nature of the pharmaceutical composition or carrier or of the diluent depends on the desired administration form. Oral compositions can be present, for example, as tablets or capsules and can contain customary excipients such as binders (e.g., syrup, acacia, gelatin, sorbitol, tragacanth or polyvinylpyrrolidone), fillers (e.g., lactose, sugar, cornstarch, calcium phosphate, sorbitol or glycine), lubricants (e.g., magnesium stearate, talc, polyethylene glycol or silicon dioxide), disintegrants (e.g., starch) or wetting agents (e.g., sodium laurylsulfate). Liquid oral preparations can be in the form of aqueous or oily suspensions, solutions, emulsions, syrups, elixirs or sprays and the like. They can also be present as a dry powder, which is prepared for reconstitution with water or another suitable carrier. Liquid preparations of this type can contain customary additives, for example suspending agents, flavorings, diluents or emulsifiers. For parenteral administration, solutions or suspensions with customary pharmaceutical carriers can be employed.

The compounds or compositions according to the invention can be administered to mammals (human or animal) in a dose of approximately 0.5 to 100 mg per kg of body weight per day. They can be given in an individual dose or in a number of doses. The spectrum of action of the compounds as inhibitors of cyclooxygenases (COX-1 and COX-2) was investigated with the aid of the test systems below.

The compounds according to the invention can also be present as pharmaceutical or cosmetic preparations for topical administration, for example in the form of emulsions, pastes, ointments, gels, creams, lotions, powders or sprays. In addition to the active compound(s), these preparations can contain customary vehicles. The preparations in the form of ointments, pastes, creams or gels can contain, for example, animal and/or vegetable fats, waxes, paraffins, starch, tragacanth, cellulose derivatives, polyethylene glycols, silicones, bentonites, silicic acid, talc and zinc oxide or mixtures thereof. In addition to the active compounds, powders and sprays can contain, for example, lactose, talc, silicic acid, aluminum hydroxide, calcium silicate and polyamide powder. Emulsions and lotions can contain customary solvents, diluents and emulsifiers.

In-vitro Test Procedure for the Determination of COX-1 Inhibition

The inhibition of the cyclooxygenase pathway is carried out by fluorimetric quantification of malonaldehyde (MA). This condenses in the acidic medium with twice the molar amount of thiobarbituric acid to give a red pigment dye, which has a fluorescence at $\lambda_{Excitation}$: 533 nm, $\lambda_{Emission}$: 550 nm.

A platelet suspension obtained from pig's blood is pre-incubated with the test substance for 10 min at 37° C. The concentration of the suspension should be $8 \times 10^8$ cells/ml. The arachidonic acid cascade is then activated by addition of the antibiotic calcium ionophore A23187 (5 mol/l). After a further 10 min at 37° C., the reaction is stopped using a trichloroacetic acid solution. The samples are centrifuged and the supernatant is incubated with thiobarbituric acid for 30 min at 70° C. After cooling (30 min at room temperature), the samples are measured fluorimetrically at 533/550 nm and the $IC_{50}$ values of the test compounds are determined therefrom by means of a calibration curve.

In-vitro Test Procedure for the Determination of COX-2 Inhibition

The procedure is carried out on LPS-stimulated human monocytes which have been obtained by Ficoll extraction. The measurement variable used is the $PGE_2$ formed, which is determined by means of ELISA.

The results of the in-vitro test for COX-1 inhibition are shown in tables 1 to 17 below.

TABLE 1

Inhibitory activities of the carbamic acid thioesters of the formula:

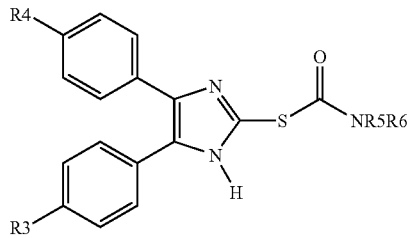

| Example | Compound | $NR^5R^6$ | $R^4$ | $R^3$ | MDA $IC_{50}$ [M] | MDA $pIC_{50}$ [M] |
|---|---|---|---|---|---|---|
| 42 | T1 | $N(CH_3)_2$ | $OCH_3$ | $OCH_3$ | $7.1 \times 10^{-8}$ | 7.15 |
| 43 | T2 | $N(C_2H_5)_2$ | $OCH_3$ | $OCH_3$ | $4.8 \times 10^{-9}$ | 8.32 |
| 44 | T3 | $N(I-C_3H_7)_2$ | $OCH_3$ | $OCH_3$ | $1.2 \times 10^{-8}$ | 7.92 |
| 45 | T4 | morpholino | $OCH_3$ | $OCH_3$ | $2.8 \times 10^{-8}$ | 7.55 |
| 68 | T103 | $N(CH_3)_2$ | Cl | H | $7.3 \times 10^{-6}$ | 5.14 |
| 69 | T104 | $N(C_2H_5)_2$ | Cl | H | $4.2 \times 10^{-6}$ | 5.38 |
| 72 | T108 | $N(C_2H_5)_2$ | Cl | $OCH_3$ | $1.6 \times 10^{-7}$ | 6.80 |

TABLE 2

Inhibitory activities of the sulfanylacetamides of the formula:

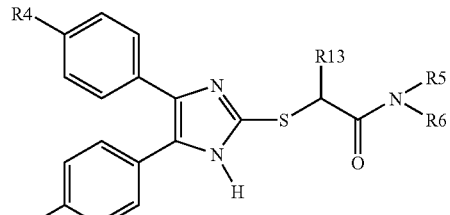

| Example | Compound | $R^6$ | $R^5$ | $R^3, R^4$ | $R^{13}$ | MDA $IC_{50}$ [M] | MDA $pIC_{50}$ [M] |
|---|---|---|---|---|---|---|---|
| 23 | T5 | H | H | $OCH_3$ | H | $4.5 \times 10^{-7}$ | 6.35 |
| 24 | T6 | $CH_3$ | $CH_3$ | $OCH_3$ | H | $1.0 \times 10^{-8}$ | 8.00 |
| 46 | T7 | $CH_3$ | $CH_3$ | $OCH_3$ | $COCH_3$ | $3.3 \times 10^{-8}$ | 7.48 |
| 47 | T9 | $C_6H_5$ | H | $OCH_3$ | H | $3.5 \times 10^{-8}$ | 7.46 |
| 48 | T10 | $4\text{-}ClC_6H_4$ | H | $OCH_3$ | H | $2.1 \times 10^{-7}$ | 6.68 |

TABLE 3

Inhibitory activities of the amines of the formula:

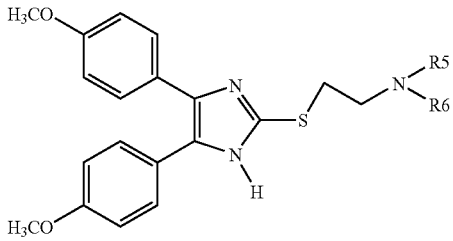

| Example | Compound | $R^5$ | $R^6$ | MDA $IC_{50}$ [M] | MDA $pIC_{50}$ [M] |
|---|---|---|---|---|---|
| 27 | T14 | $CH_3$ | $CH_3$ | $3.2 \times 10^{-6}$ | 5.49 |
| 28 | T15 | H | H | $7.8 \times 10^{-8}$ | 6.11 |

TABLE 4

Inhibitory activities of the aryl ketones of the formula:

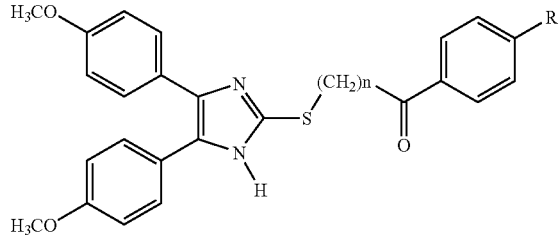

| Example | Compound | R | n | MDA IC$_{50}$ [M] | MDA pIC$_{50}$ [M] |
|---|---|---|---|---|---|
| 25 | T11 | H | 1 | $9.5 \times 10^{-9}$ | 8.02 |
| 26 | T12 | Cl | 1 | $4.6 \times 10^{-8}$ | 7.34 |
| 49 | T13 | H | 2 | $2.1 \times 10^{-8}$ | 7.68 |

TABLE 5

Inhibitory activities of the heteroarylmethyl sulfides of the formula:

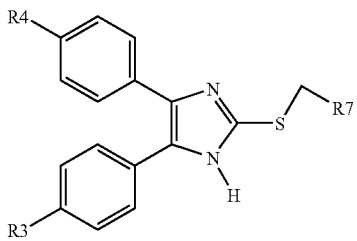

| Example | Compound | R$^7$ | R$^4$ | R$^3$ | MDA IC$_{50}$ [M] | MDA pIC$_{50}$ [M] |
|---|---|---|---|---|---|---|
| 30 | T69 | 2-pyridyl | OCH$_3$ | OCH$_3$ | $1.0 \times 10^{-7}$ | 7.00 |
| 31 | T70 | 3-pyridyl | OCH$_3$ | OCH$_3$ | $3.0 \times 10^{-9}$ | 8.52 |
| 32 | T71 | 4-pyridyl | OCH$_3$ | OCH$_3$ | $3.0 \times 10^{-9}$ | 8.52 |
| 33 | T72 | 2-quinolyl | OCH$_3$ | OCH$_3$ | $9.0 \times 10^{-8}$ | 7.05 |
| 34 | T73 | 2-benzimidazolyl | OCH$_3$ | OCH$_3$ | $3.9 \times 10^{-7}$ | 6.41 |
| 36 | T83 | 2-pyridyl | Cl | Cl | $3.3 \times 10^{-7}$ | 6.48 |
| 38 | T91 | 2-pyridyl | H | H | $7.0 \times 10^{-7}$ | 6.15 |

TABLE 6

Inhibitory activities of the N$^1$-acetic acid derivatives of the formula:

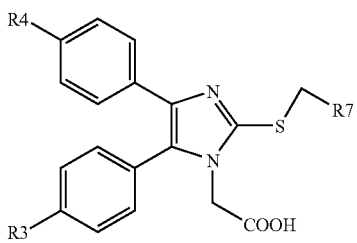

| Example | Compound | R$^7$ | R$^4$ | R$^3$ | MDA IC$_{50}$ [M] | MDA pIC$_{50}$ [M] |
|---|---|---|---|---|---|---|
| 130 | T77 | 4-pyridyl | OCH$_3$ | OCH$_3$ | $7.2 \times 10^{-7}$ | 6.14 |
| 133 | T109 | 2-pyridyl | Cl | OCH$_3$ | $4.9 \times 10^{-7}$ | 6.31 |

TABLE 7

Inhibitory activities of the arylamides of the formula:

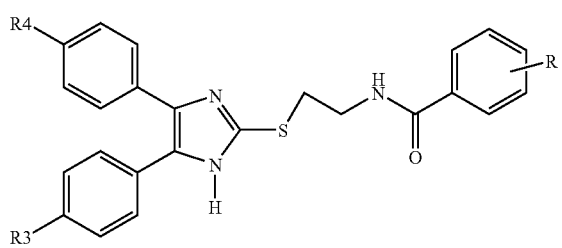

| Example | Compound | R$^7$ | R$^4$ | R$^3$ | MDA IC$_{50}$ [M] | MDA pIC$_{50}$ [M] |
|---|---|---|---|---|---|---|
| 29 | T28 | H | OCH$_3$ | OCH$_3$ | $5.4 \times 10^{-7}$ | 6.27 |
| 86 | T32 | 4-Cl | OCH$_3$ | OCH$_3$ | $2.5 \times 10^{-7}$ | 6.60 |
| 87 | T33 | 3-Cl | OCH$_3$ | OCH$_3$ | $9.3 \times 10^{-7}$ | 6.03 |
| 88 | T34 | 2-Cl | OCH$_3$ | OCH$_3$ | $6.2 \times 10^{-8}$ | 7.21 |
| 89 | T35 | 2,4-diCl | OCH$_3$ | OCH$_3$ | $1.5 \times 10^{-7}$ | 6.82 |
| 90 | T36 | 2,6-diCl | OCH$_3$ | OCH$_3$ | $1.1 \times 10^{-7}$ | 6.96 |
| 91 | T37 | 3,5-diCl | OCH$_3$ | OCH$_3$ | $5.2 \times 10^{-7}$ | 6.28 |
| 92 | T38 | 4-F | OCH$_3$ | OCH$_3$ | $2.5 \times 10^{-7}$ | 6.60 |
| 93 | T39 | 4-ON | OCH$_3$ | OCH$_3$ | $1.4 \times 10^{-7}$ | 6.85 |
| 94 | T40 | 4-NO$_2$ | OCH$_3$ | OCH$_3$ | $8.1 \times 10^{-8}$ | 7.09 |
| 95 | T41 | 2-NO$_2$ | OCH$_3$ | OCH$_3$ | $1.7 \times 10^{-7}$ | 6.77 |
| 96 | T42 | 4-CF$_3$ | OCH$_3$ | OCH$_3$ | $3.2 \times 10^{-7}$ | 6.49 |
| 97 | T43 | 3-CF$_3$ | OCH$_3$ | OCH$_3$ | $1.0 \times 10^{-7}$ | 7.00 |
| 98 | T44 | 3,5-diCF$_3$ | OCH$_3$ | OCH$_3$ | $5.2 \times 10^{-7}$ | 6.28 |
| 99 | T45 | 4-OCH$_3$ | OCH$_3$ | OCH$_3$ | $1.0 \times 10^{-6}$ | 6.00 |
| 100 | T46 | 3,4,5-triOCH$_3$ | OCH$_3$ | OCH$_3$ | $6.4 \times 10^{-7}$ | 6.22 |
| 101 | T47 | 4-CH$_3$ | OCH$_3$ | OCH$_3$ | $1.4 \times 10^{-7}$ | 6.85 |
| 102 | T48 | 4-tertC$_4$H$_9$ | OCH$_3$ | OCH$_3$ | $8.2 \times 10^{-8}$ | 7.09 |
| 56 | T85 | H | Cl | Cl | $4.5 \times 10^{-7}$ | 6.35 |
| 61 | T94 | H | H | H | $2.1 \times 10^{-6}$ | 5.68 |
| 64 | T98 | H | F | F | $1.0 \times 10^{-6}$ | 6.00 |
| 70 | T106 | H | Cl | H | $9.0 \times 10^{-7}$ | 6.05 |
| 73 | T110 | H | Cl | OCH$_3$ | $3.3 \times 10^{-6}$ | 5.48 |

TABLE 8

Inhibitory activities of the arylsulfonamides of the formula:

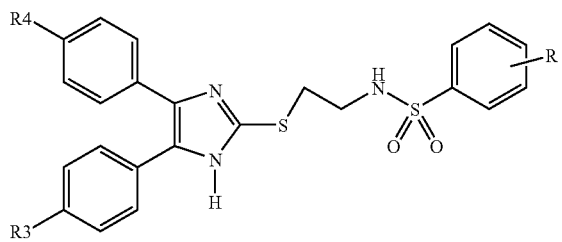

| Example | Compound | R | R$^4$ | R$^3$ | MDA IC$_{50}$ [M] | MDA pIC$_{50}$ [M] |
|---|---|---|---|---|---|---|
| 76 | T17 | H | OCH$_3$ | OCH$_3$ | $5.0 \times 10^{-8}$ | 7.30 |
| 50/77 | T18 | 4-Cl | OCH$_3$ | OCH$_3$ | $2.8 \times 10^{-7}$ | 6.55 |
| 78 | T20 | 4-F | OCH$_3$ | OCH$_3$ | $6.0 \times 10^{-8}$ | 7.22 |
| 79 | T21 | 2-NO$_2$ | OCH$_3$ | OCH$_3$ | $1.1 \times 10^{-7}$ | 6.96 |

TABLE 8-continued

Inhibitory activities of the arylsulfonamides of the formula:

| Example | Compound | R | $R^4$ | $R^3$ | MDA $IC_{50}$ [M] | MDA $pIC_{50}$ [M] |
|---|---|---|---|---|---|---|
| 80 | T22 | 3,5-diCF$_3$ | OCH$_3$ | OCH$_3$ | $4.1 \times 10^{-7}$ | 6.39 |
| 82 | T24 | 4-CH$_3$ | OCH$_3$ | OCH$_3$ | $4.8 \times 10^{-8}$ | 7.32 |
| 83 | T25 | 2,4,6-triCH$_3$ | OCH$_3$ | OCH$_3$ | $3.2 \times 10^{-7}$ | 6.49 |
| 84 | T26 | 4-tertC$_4$H$_9$ | OCH$_3$ | OCH$_3$ | $4.9 \times 10^{-7}$ | 6.31 |
| 85 | T27 | 4-NHCOCH$_3$ | OCH$_3$ | OCH$_3$ | $1.8 \times 10^{-8}$ | 7.74 |
| 74 | T111 | 4-Cl | Cl | OCH$_3$ | $1.3 \times 10^{-7}$ | 6.89 |

TABLE 9

Inhibitory activities of the alkylamides of the formula:

| Example | Compound | $R^{11}$ | $R^4$ | $R^3$ | MDA $IC_{50}$ [M] | MDA $pIC_{50}$ [M] |
|---|---|---|---|---|---|---|
| 52 | T49 | CH$_3$ | OCH$_3$ | OCH$_3$ | $1.0 \times 10^{-8}$ | 8.00 |
| 103 | T50 | CH$_2$CH$_3$ | OCH$_3$ | OCH$_3$ | $4.7 \times 10^{-8}$ | 7.33 |
| 104 | T51 | CH(CH$_3$)$_2$ | OCH$_3$ | OCH$_3$ | $8.8 \times 10^{-9}$ | 8.06 |
| 105 | T52 | C(CH$_3$)$_3$ | OCH$_3$ | OCH$_3$ | $4.2 \times 10^{-7}$ | 6.38 |
| 112 | T59 | CH$_2$Ph | OCH$_3$ | OCH$_3$ | $5.4 \times 10^{-8}$ | 7.27 |
| 113 | T60 | CH$_2$Ph | OCH$_3$ | OCH$_3$ | $1.5 \times 10^{-7}$ | 8.82 |
| 114 | T61 | CH=CHPh | OCH$_3$ | OCH$_3$ | $1.8 \times 10^{-7}$ | 6.74 |
| 115 | T62 | CH(Ph)$_2$ | OCH$_3$ | OCH$_3$ | $1.3 \times 10^{-7}$ | 6.89 |
| 55 | T84 | CH$_3$ | Cl | Cl | $1.1 \times 10^{-8}$ | 5.96 |

TABLE 10

Inhibitory activities of the alkylsulfonamides of the formula:

| Example | Compound | $R^{12}$ | $R^4$ | $R^3$ | MDA $IC_{50}$ [M] | MDA $pIC_{50}$ [M] |
|---|---|---|---|---|---|---|
| 116 | T63 | CH$_3$ | OCH$_3$ | OCH$_3$ | $7.6 \times 10^{-8}$ | 7.12 |
| 117 | T64 | CH$_2$CH$_3$ | OCH$_3$ | OCH$_3$ | $3.9 \times 10^{-8}$ | 7.41 |
| 118 | T65 | CH(CH$_3$)$_2$ | OCH$_3$ | OCH$_3$ | $1.0 \times 10^{-8}$ | 8.00 |
| 119 | T66 | CH$_2$Ph | OCH$_3$ | OCH$_3$ | $1.0 \times 10^{-7}$ | 7.00 |

TABLE 11

Inhibitory activities of the heteroaryl- and naphthylamides of the formula:

| Example | Compound | $R^{11}$ | $R^4$ | $R^3$ | MDA $IC_{50}$ [M] | MDA $pIC_{50}$ [M] |
|---|---|---|---|---|---|---|
| 106 | T53 | 2-furyl | OCH$_3$ | OCH$_3$ | $3.5 \times 10^{-7}$ | 6.46 |
| 107 | T54 | 2-thienyl | OCH$_3$ | OCH$_3$ | $1.0 \times 10^{-7}$ | 7.00 |
| 108 | T55 | 1-naphthyl | OCH$_3$ | OCH$_3$ | $5.6 \times 10^{-7}$ | 6.25 |
| 109 | T56 | 2-naphthyl | OCH$_3$ | OCH$_3$ | $4.0 \times 10^{-8}$ | 7.40 |

TABLE 12

Inhibitory activities of the naphthylsulfonamides of the formula:

| Example | Compound | $R^{12}$ | $R^4$ | $R^3$ | MDA $IC_{50}$ [M] | MDA $pIC_{50}$ [M] |
|---|---|---|---|---|---|---|
| 120 | T67 | 1-naphthyl | OCH$_3$ | OCH$_3$ | $3.8 \times 10^{-7}$ | 6.42 |
| 121 | T68 | 2-naphthyl | OCH$_3$ | OCH$_3$ | $1.3 \times 10^{-7}$ | 6.89 |

TABLE 13

Inhibitory activities of the urea derivatives of the formula:

[Structure: 4,5-bis(4-methoxyphenyl)-imidazole with S-CH2CH2-NH-C(=O)-N(R5)(R6)]

| Example | Compound | $R^5$, $R^6$ | MDA $IC_{50}$ [M] | MDA $pI_{50}$ [M] |
|---|---|---|---|---|
| 110 | T57 | $CH_3$ | $7.8 \times 10^{-8}$ | 7.11 |
| 111 | T58 | $C_2H_3$ | $5.0 \times 10^{-8}$ | 7.30 |

TABLE 14

Inhibitory activities of the sulfones and their sulfide analogs of the formula:

[Structure: 4,5-bis(4-methoxyphenyl)-imidazole with S(O)n-CH2-R7]

| Example | Compound | $R^7$ | n | MDA $IC_{50}$ [M] | MDA $pIC_{50}$ [M] |
|---|---|---|---|---|---|
|  | T69 | 2-pyridyl | 0 | $1.0 \times 10^{-7}$ | 7.00 |
| 134 | T74 | 2-pyridyl | 2 | $8.1 \times 10^{-8}$ | 7.09 |
| 30 | T79 | $COOC_2H_5$ | 0 | $1.2 \times 10^{-8}$ | 7.92 |
| 135 | T80 | $COOC_2H_5$ | 2 | $7.5 \times 10^{-9}$ | 8.12 |

TABLE 15

Inhibitory activities of the N,N-acetamides of the formula:

[Structure: 4,5-bis(4-R3/R4-phenyl)-imidazole with S-CH(R13)-C(=O)-N(R5)(R6)]

| Example | Compound | $R^{13}$ | $R^3$, $R^4$ | MDA $IC_{50}$ [M] | MDA $pIC_{50}$ [M] |
|---|---|---|---|---|---|
| 24 | T6 | H | $OCH_3$ | $1.0 \times 10^{-8}$ | 8.00 |
| 135 | T8 | $CH_3$ | $OCH_3$ | $4.2 \times 10^{-7}$ | 6.38 |

TABLE 15-continued

Inhibitory activities of the N,N-acetamides of the formula:

| Example | Compound | $R^{13}$ | $R^3$, $R^4$ | MDA $IC_{50}$ [M] | MDA $pIC_{50}$ [M] |
|---|---|---|---|---|---|
| 37 | T87 | H | Cl | $1.5 \times 10^{-6}$ | 5.82 |
| 139 | T88 | $CH_3$ | Cl | $5.2 \times 10^{-6}$ | 5.28 |

TABLE 16

Inhibitory activities of the dimethyl compounds of the formula:

[Structure: 4,5-bis(4-methoxyphenyl)-N-R2-imidazole with S-CH2CH2-N(R10)-Y-phenyl-R]

| Example | Compound | $R^2$, $R^{10}$ | R | Y | MDA $IC_{50}$ [M] | MDA $pIC_{50}$ [M] |
|---|---|---|---|---|---|---|
| 138 | T31 | $CH_3$ | H | C=O | $8.4 \times 10^{-7}$ | 7.08 |
| 137 | T19 | $CH_3$ | Cl | $SO_2$ | $6.9 \times 10^{-7}$ | 7.16 |

TABLE 17

Inhibitory activities of the methyl derivatives of the formula:

[Structure: 4,5-bis(4-methoxyphenyl)-N-R2-imidazole with S-CH2CH2-N(R10)-C(=O)-phenyl]

| Example | Compound | $R^{10}$ | $R^2$ | MDA $IC_{50}$ [M] | MDA $pIC_{50}$ [M] |
|---|---|---|---|---|---|
| 140 | T29 | $CH_3$ | H | $2.1 \times 10^{-8}$ | 7.68 |
| 51 | T30 | H | $CH_3$ | $4.2 \times 10^{-8}$ | 7.38 |

Particularly suitable compounds according to the invention are the compounds T2, T11, T51, T70, T71 and T80 having $IC_{50}$ values in the molar region of $10^{-9}$. These compounds show a particularly high activity for the inhibition of cyclooxygenase-1.

The results of the in-vitro tests for COX-2 inhibition are shown in table 18 below.

TABLE 18

COX-2 inhibition by compounds of the formula:

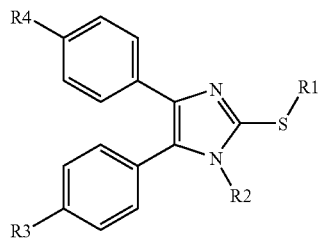

| Example | No. | $R^4$ | $R^3$ | $R^1$ | $R^2$ | $IC_{50}$ [M] | $pIC_{50}$ [M] |
|---|---|---|---|---|---|---|---|
| 43 | T2 | $OCH_3$ | $OCH_3$ | $CON(C_2H_5)_2$ | H | $2.4 \times 10^{-6}$ | 5.62 |
| 24 | T6 | $OCH_3$ | $OCH_3$ | $CH_2CON(CH_3)_2$ | H | $2.3 \times 10^{-6}$ | 5.64 |
| 46 | T7 | $OCH_3$ | $OCH_3$ | $CH(COCH_3)CON(CH_3)_2$ | H | $5.0 \times 10^{-7}$ | 6.30 |
| 25 | T11 | $OCH_3$ | $OCH_3$ | $CH_2COPh$ | H | $2.6 \times 10^{-7}$ | 6.59 |
| 50/77 | T18 | $OCH_3$ | $OCH_3$ | $CH_2CH_2NHSO_2Ph$-4Cl | H | $3.0 \times 10^{-6}$ | 5.52 |
| 80 | T22 | $OCH_3$ | $OCH^3$ | $CH_2CH_2NHSO_2Ph$-3,5-$diCF_3$ | H | $1.5 \times 10^{-6}$ | 5.82 |
| 85 | T27 | $OCH_3$ | $OCH_3$ | $CH_2CH_2NHSO_2Ph$-4NHCOCH_3 | H | $1.2 \times 10^{-6}$ | 5.92 |
| 140 | T29 | $OCH_3$ | $OCH_3$ | $CH_2CH_2N(CH_3)COPh$ | H | $1.0 \times 10^{-8}$ | 8.00 |
| 138 | T31 | $OCH_3$ | $OCH_3$ | $CH_2CH_2N(CH_3)COPh$ | $CH_3$ | $9.1 \times 10^{-7}$ | 6.04 |
| 52 | T49 | $OCH_3$ | $OCH_3$ | $CH_2CH_2NHCOCH_3$ | H | $2.7 \times 10^{-6}$ | 5.57 |
| 110 | T57 | $OCH_3$ | $OCH_3$ | $CH_2CH_2NHCON(CH_3)_2$ | H | $2.1 \times 10^{-7}$ | 6.68 |
| 30 | T69 | $OCH_3$ | $OCH_3$ | 2-pyridylmethyl | H | $2.4 \times 10^{-7}$ | 6.62 |
| 55 | T84 | Cl | Cl | $CH_2CH_2NHCOCH_3$ | H | $2.7 \times 10^{-6}$ | 5.57 |
| 72 | T108 | Cl | $OCH_3$ | $CON(C_2H_5)_2$ | H | $1.0 \times 10^{-6}$ | 6.00 |
| 133 | T109 | Cl | $OCH_3$ | 2-pyridylmethyl | $CH_2$ | $1.0 \times 10^{-6}$ | 6.00 |
| 74 | T111 | Cl | $OCH_3$ | $CH_2CH_2NHSO_2Ph$-4Cl | H | $8.0 \times 10^{-7}$ | 6.10 |

It has been found that the compound T29 according to the invention inhibits both isoenzymes, COX-1 and COX-2, with approximately equally high potency. A medium-strong inhibition for both enzymes was observed with the compound T 109.

The compounds according to the invention and the processes for their preparation are now described in greater detail by examples below, which do not restrict the invention in any manner.

EXAMPLES

In the examples, the syntheses of the intermediate compounds Z1 to Z22 named by Z, from which the compounds T1 to T111 according to the invention were obtained, are described first.

a) Synthesis of symmetrical benzoins

Example 1

Synthesis of 1,2-bis(4-chlorophenyl)-2-hydroxy-ethanone (4,4'-dichloro-benzoin) (Z1)

42.2 g of 4-chlorobenzaldehyde and 5 g of KCN were heated under reflux in 300 ml of a 1:1 mixture of ethanol and water for 6 hours. After cooling, the ethanol was stripped off, the residue was cooled in an ice bath and the supernatant aqueous phase was decanted off. The product was recrystallized from ethanol/petroleum ether and dried. 22 g of the compound Z1 mentioned in the title were obtained.

Example 2

Synthesis of 1,2-bis(4-fluorophenyl)-2-hydroxyethanone (4,4'-dichloro-benzoin) (Z2)

50 g of 4-fluorobenzaldehyde were reacted by the same process as in example 1. 29 g were obtained.

Example 3

Synthesis of 1,2-bis[4-(trifluoromethyl)phenyl]-2-hydroxyethanone (4,4'-trifluoromethylbenzoin) (Z3)

50 g of 4-fluorobenzaldehyde were reacted by the same process as in example 1. The yield was 28 g.

b) Synthesis of unsymmetrical benzoins

Example 4

Synthesis of 2-phenyl-1,3-dithiane (Z4)

26.5 g (0.25 mol) of benzaldehyde and 27.1 g (0.25 mol) of propanedithiol were dissolved in chloroform and cooled in an ice bath. HCl gas was then passed in for approximately 5 min until saturation and the solution was allowed to stand at RT (room temperature). The reaction mixture was washed twice with 100 ml of water, three times with 100 ml of 10% strength KOH solution and twice again with 100 ml of water. The organic phases were dried using $Na_2SO_4$, evaporated in a rotary evaporator and recrystallized from methanol. The yield was 34.9 g.

Example 5

Synthesis of 2-(4-chlorophenyl)-1,3-dithiane (Z5)

34 g (0.24 mol) of 4-chlorobenzaldehyde were reacted with the same molar amount of propanedithiol by the process as described in example 4. The yield was 48.64 g.

Example 6

Synthesis of 2-chlorophenyl-(2-phenyl-1,3-dithian-2-yl)methanol (Z6)

33.0 g (0.169 mol) of the compound Z4 from example 4 were dissolved in dry THF and cooled to −60° C. 112 ml (0.178 mol) of n-butyllithium (BuLi) were then added under nitrogen and the reaction mixture was stirred in the cold for 15-30 min. 24.0 g (0.169 mol) of 4-chlorobenzaldehyde were added and the mixture was stirred at RT for 1 hour. The THF (tetrahydrofuran) was then stripped off, the residue was treated with water and the mixture was extracted four times with $CH_2Cl_2$. The organic phase was washed twice each with water, 7% strength KOH and again with water, dried using $Na_2SO_4$ and evaporated in a rotary evaporator. The yield was 48.5 g.

Example 7

Synthesis of 2-(4-chlorophenyl)-1,3-dithian-2-yl-4-methoxyphenyl-methanol (Z7)

47 g (0.204 mol) of the compound Z 5 from example 5 and the same molar amount of 4-methoxybenzaldehyde were reacted together with 112 ml (0.178 mol) of BuLi as in example 6. The yield of the compound named in the title was 64.2 g.

Example 8

Synthesis of 2-(4-chlorophenyl)-2-hydroxy-1-phenylethan-1-one (Z8)

46.6 g (0.138 mol) of the compound Z6 was heated under reflux for 5 hours with 80.0 g (0.295 mol) of $HgCl_2$ and 40.0 g (0.185 mol) of HgO in 600 ml of 90% strength methanol. The solids were filtered off and washed with $CH_2Cl_2$ and diethyl ether. The filtrate was evaporated, the residue was treated with water and the mixture was extracted four times with diethyl ether. The combined organic phases were washed successively with water, 5% strength $NH_4Cl$ solution and again with water, dried over $Na_2SO_4$, evaporated in a rotary evaporator and recrystallized from petroleum ether. The yield was 24.8 g.

Example 9

Synthesis of 2-(4-chlorophenyl)-2-hydroxy-(4-methoxyphenyl)ethan-1-one (Z9)

64.2 g (0.175 mol) of the compound Z7 were reacted as in example 8. The yield was 35.89 g.

c) Synthesis of the 4,5-diaryl-1H-imidazole-2-thiols

Example 10

Synthesis of 4,5-diphenyl-1H-imidazole-2-thiol (Z10)

21.2 g (0.10 mol) of benzoin were dissolved in DMF (dimethylformamide) with 10.8 g (0.15 mol) of thiourea with warming and the mixture was heated under reflux for 15 hours. After cooling, the DMF was stripped off and the residue was treated with ethanol. The precipitate resulting in the course of this was filtered off with suction, washed with cold ethanol, dried and reused without further purification. The yield was 18.4 g.

Example 11

Synthesis of 4,5-bis(4-methoxyphenyl)-1H-imidazole-2-thiol (Z11)

27.23 g (0.1 mol) of p-anisoin and 10.8 g (0.15 mol) of thiourea were reacted as in example 10. The yield was 20 g.

Example 12

Synthesis of 4,5-bis(4-chlorophenyl)-1H-imidazole-2-thiol (Z12)

22 g (78.5 mol) of the compound Z1 from example 1 and 12 g (157 mol) of thiourea were reacted as in example 10. The yield was 15.7 g.

Example 13

Synthesis of 4,5-bis(4-fluorophenyl)-1H-imidazole-2-thiol (Z13)

29 g (0.12 mol) of the compound Z2 from example 2 and 18 g (0.24 mol) of thiourea were reacted as in example 10. The yield was 17.9 g.

Example 14

Synthesis of 4,5-bis [4-(trifluoromethyl)phenyl)-1H-imidazole-2-thiol (Z14)

28g (0. 08 mol) of the compound Z3 from example 3 and 12 g (0.16 mol) of thiourea were reacted as in example 10. The yield was 7.4 g.

Example 15

Synthesis of 4,5-bis(4-methoxyphenyl)-1-methyl-1H-imidazole-2-thiol (Z15)

13.6 g (50 mmol) of p-anisoin and 6.8 g (75 mmol) of N-methylthiourea were reacted as in example 10. The yield was 7.4 g.

Example 16

Synthesis of 4-(4-chlorophenyl)-5-phenyl-1H-imidazole-2-thiol (Z16)

24.8 g (0.10 mol) of the compound Z8 from example 8 and 10.8 g (0.15 mol) of thiourea were reacted as in example 10. The yield was 11.3 g.

Example 17

Synthesis of 4-(4-chlorophenyl)-5-(4-methoxyphenyl)-1H-imidazole-2-thiol (Z17)

35.9 g (0.13 mol) of the compound Z9 from example 9 and 15.2 g (0.20 mol) of thiourea were reacted as in example 10. The yield was 17 g.

d) Synthesis of $N^1$-(4-chlorophenyl)-2-chloroacetamide

Example 18

Synthesis of $N^1$-(4-chlorophenyl)-2-chloroacetamide (Z18)

3.4 g (30 mol) of 2-chloroacetyl chloride were dissolved in anhydrous dioxane and a solution containing 3.8 g (30 mol) of 4-chloroaniline was added dropwise. After an hour, the batch was poured into ice water, acidified using dilute hydrochloric acid, the supernatant was removed by suction and the residue was washed with water until neutral. The reaction product was recrystallized from ethanol. The yield was 3.2 g.

e) Synthesis of $N^1$-(2-halophenyl)-4-chlorobenzenesulphonamides

Example 19

Synthesis of N-hu 1-(2-chloroethyl)-4-chlorobenzenesulfonamide (Z19)

11.6 g (100 mmol) of 2-chloroethylamine HCl were suspended in dichloromethane. 13.8 g (175 mmol) of pyridine were added, the mixture was stirred for 10 minutes and then 15.8 g (75 mmol) of 4-chlorobenzenesulfonyl chloride, dissolved in dichloro-methane, were added dropwise. The reaction mixture was heated under reflux for 8-10 hours, then treated with water and adjusted to a pH of 1-2 using HCl. The organic phase was washed three times with 3% strength HCl and the aqueous phase was extracted by shaking 3-4 times with dichloromethane. The combined organic phases were dried using $Na_2SO_4$, evaporated in the and recrystallized from ethanol. The yield was 11 g.

Example 20

Synthesis of $N^1$-(2-bromoethyl)-4-chlorobenzenesulfonamide (Z20)

15.4 g (75 mmol) of 2-bromoethylamine HBr, 11.8 g (150 mmol) of pyridine and 10.6 g (50 mmol) of 4-chlorobenzenesulfonyl chloride were reacted as in example 19. The yield was 6.5 g.

f) Compounds which were obtained by nucleophilic substitution of the 4,5-diaryl-1H-imidazole-2-thiols in the 2-position with the aid of a sodium methoxide solution

Example 21

Synthesis of 2-[4,5-bis(4-methoxyphenyl)-1H-imidazol-2-ylsulfanyl]-propanamine (Z21)

Dry methanol was slowly added dropwise to 1.0 g (42 mmol) of initially introduced $Na^0$ such that the solution boiled moderately. 5.0 g (16 mmol) of the compound Z11 from example 11 were added and the reaction mixture was stirred at RT for 10 min. 3.5 g (16 mmol) of 3-bromopropylamine HBr, dissolved in methanol, were then added and the mixture was heated under reflux for 2 h. After cooling, the product was worked up by stripping of the methanol, treating the residue with dichloromethane and washing it with 1 N NaOH and water. The organic phase was dried over $Na_2SO_4$ and evaporated. The yield was 3.5 g.

Example 22

Synthesis of 2-[4-(4-chlorophenyl)-5-(4-methoxyphenyl)-1H-imidazol-2-ylsulfanylmethyl]pyridine (Z22)

387 mg (16.8 mmol) of $Na^0$, 2.5 g (7.89 mmol) of the compound Z17 from example 17 and 1.3 g (7.89 mmol) of 2-chloromethylpyridine HCl were reacted as in example 21. Working-up was carried out by means of column chromatography on silica gel, eluting with ethyl acetate. The yield was 1.77 g.

Example 23

Synthesis of 2-[4,5-bis(4-methoxyphenyl)-1H-imidazol-2-ylsulfanyl]-acetamide (T5)

213 mg (10 mmol) of $Na^0$, 2.5 g (8 mmol) of the compound Z11 from example 11 and 748 g (8 mmol) of 2-chloroacetamide were reacted as in example 21. Working-up was carried out by means of column chromatography on silica gel, eluting with ethyl acetate. 0.8 g of the compound named in the title was obtained. IR (KBr): $1/\lambda$ (cm$^{-1}$)=1670, 1610, 1500, 1440, 1240

In an analogous manner to that described in example 23, the compounds below were prepared from the starting materials mentioned:

Example 24

$N^1N^1$-Dimethyl-2-[4,5-bis(4-methoxyphenyl)-1H-imidazol-2-ylsulfanyl]-acetamide (T6)

Starting substances: 3.0 g (9.6 mmol) of Z11; 1.2 g (9.6 mmol) of 2-chloro-N,N-di-methylacetamide; 230 mg (10 mmol) of $Na^0$ Yield: 1.8 g IR (KBr): $1/\lambda$ (cm$^{-1}$)=2820, 1620, 1500, 1455, 1240, 830

Example 25

2-[4,5-Bis(4-methoxyphenyl)-1H-imidazol-2-ylsulfanyl]-1-phenylethan-1-one (T11)

Starting substances: 2.5 g (8 mmol) of Z11; 748 mg (8 mmol) of ω-bromo-acetophenone; 230 mg (10 mmol) of $Na^0$ Eluent: ethyl acetate/dichloromethane 1:3

Yield: 0.9 g IR (KBr): $1/\lambda$ (cm$^{-1}$)=1680, 1610, 1590, 1500, 1445, 1245, 830, 750, 690

Example 26

2-[4,5-Bis(4-methoxyphenyl)-1H-imidazol-2-ylsulfanyl-1-(4-chloro-phenyl)ethan-1-one (T12)

Starting substances: 3.0 g (9.6 mmol) of Z11; 2.2 g (9.6 mmol) of ω-bromo-4-chloro-acetophenone; 0.3 g (13 mmol) of $Na^0$ Eluent: ethyl acetate/dichloromethane 1:3

Yield: 2.3 g IR (KBr): $1/\lambda$ (cm$^{-1}$)=1680, 1610, 1585, 1500, 1460, 1245, 835

Example 27

N,N-Dimethyl-[4,5-bis(4-methoxyphenyl)-1H-imidazol-2-ylsulfanyl]-ethanamine (T14)

Starting substances: 5.0 g (16 mmol) of Z11; 2.3 g (16 mmol) of N,N-dimethyl-2-chloroethanamine HCl; 0.8 g (35 mmol) of Na$^0$ Work-up: the precipitate was filtered off with suction and discarded. The filtrate was evaporated and purified on a silica gel column, eluting with NH$_3$/methanol/acetone/toluene.

Yield: 1.8 g IR (KBr): $1/\lambda$ (cm$^{-1}$)=2820, 1610, 1570, 1500, 1465, 1240, 830

Example 28

2-[4,5-Bis(4-methoxyphenyl)-1H-imidazol-2-ylsufanyl]ethanamine (T15)

Starting substances: 10.0 g (32 mmol) of Z11; 7.71 g (32 mmol) of 2-chloroethylamine HCl; 1.91 g (83 mmol) of Na$^0$ Work-up: the precipitate was filtered off with suction and discarded. The filtrate was evaporated, the residue was treated with 10% strength HCl and washed a number of times with dichloromethane. The aqueous phase was rendered alkaline using 10% strength KOH and extracted by shaking a number of times with diethyl ether and dichloromethane. The combined organic phases were dried using Na$_2$SO$_4$ and evaporated. The product was crystallized from diethyl ether.

Yield: 5.9 g IR (KBr): $1/\lambda$ (cm$^{-1}$)=1610, 1570, 1500, 1455, 1240, 830

Example 29

N$^1$-{2-[4,5-Bis(4-methoxyphenyl)-1H-imidazol-2-ylsufanyl]ethyl}benzamide (T28)

Starting substances: 3.0 g (9.6 mmol) of Z11; 1.8 g (9.6 mmol) of N-(2-chloroethyl)-benzamide; 230 mg (10 mmol) of Na$^0$ Eluent: ethyl acetate/dichloromethane 5:1

Yield: 0.44 g IR (KBr): $1/\lambda$ (cm$^{-1}$)=1635, 1610, 1500, 1460, 1240, 830, 710, 690

Example 30

2-[4,5-Bis(4-methoxyphenyl)-1H-imidazol-2-ylsulfanylmethyl]pyridine (T69)

Starting substances: 2.9 g (9.1 mmol) of Z11; 1.5 g (9.1 mmol) of 2-chloromethylpyridine HCl; 460 mg (20 mmol) of Na$^0$ Work-up: the precipitate was filtered off with suction, washed using methanol and discarded. The filtrate was evaporated and the residue was purified on a silica gel column, eluting with ethyl acetate.

Yield: 2.2 g IR (KBr): $1/\lambda$ (cm$^{-1}$)=1610, 1590, 1500, 1440, 1250, 840, 800, 750

Example 31

3-[4,5-Bis(4-methoxyphenyl)-1H-imidazol-2-ylsulfanylmethyl]pyridine (T70)

Starting substances: 2.9 g (9.1 mmol) of Z11; 1.5 g (9.1 mmol) of 2-chloromethylpyridine HCl; 460 mg (20 mmol) of Na$^0$ Work-up: the precipitate was filtered off with suction, washed using methanol and discarded. The filtrate was evaporated and the residue was purified on a silica gel column, eluting with ethyl acetate.

Yield: 1.95 g IR (KBr): $1/\lambda$ (cm$^{-1}$)=1610, 1575, 1500, 1460, 1250, 830, 800, 710

Example 32

4-[4,5-Bis(4-methoxyphenyl)-1H-imidazol-2-ylsulfanylmethyl]pyridine (T71)

Starting substances: 2.9 g (9.1 mmol) of Z11; 1.5 g (9.1 mmol) of 2-chloromethyl-pyridine HCl; 460 mg (20 mmol) of Na$^0$ Work-up: the precipitate was filtered off with suction, washed using methanol and discarded. The filtrate was evaporated and the residue was purified on a silica gel column, eluting with ethyl acetate.

Yield: 2.06 g IR (KBr): $1/\lambda$ (cm$^{-1}$)=1610, 1555, 1490, 1440, 1210, 840, 760, 670

Example 33

2-[4,5-Bis(4-methoxyphenyl)-1H-imidazol-2-ylsulfanylmethyl]quinoline (T72)

Starting substances: 1.5 g (4.8 mmol) of Z11; 1.0 g (4.8 mmol) of 2-chloromethyl-quinoline HCl; 176 mg (12 mmol) of Na$^0$ Work-up: the methanol was stripped off, the residue was washed using water and the product was recrystallized from ethyl acetate.

Yield: 1 g IR (KBr): $1/\lambda$ (cm$^{-1}$)=1610, 1590, 1500, 1440, 1240, 830, 800, 775

Example 34

2-[4,5-Bis(4-methoxyphenyl)-1H-imidazol-2-ylsulfanylmethyl]-1H-indole (T73)

Starting substances: 1.5 g (4.8 mmol) of Z11; 0.8 g (4.8 mmol) of 2-chloromethylindole HCl; 176 mg (12 mmol) of Na$^0$ Work-up: the precipitate was filtered off with suction, washed using methanol and discarded. The filtrate was evaporated, treated with water and extracted by shaking with CH$_2$Cl$_2$ and ethyl acetate. The organic phase was dried over Na$_2$SO$_4$, evaporated and the residue was crystallized from CH$_2$Cl$_2$.

Yield: 166 mg IR (KBr): $1/\lambda$ (cm$^{-1}$)=1615, 1525, 1505, 1250, 840

Example 35

Ethyl 2-[4,5-bis(4-methoxyphenyl)-1H-imidazol-2-ylsufanyl]acetate (T79)

Starting substances: 2.5 g (8.1 mmol) of Z11; 1.4 G. (8.1 mmol) of ethyl bromoacetate; 230 mg (10 mmol) of Na$^0$
Eluent: ethyl acetate/dichloromethane 1:3
Yield: 2.2 g IR (KBr): $1/\lambda$ (cm$^{-1}$)=2950, 1740, 1610, 1570, 1500, 1460, 1250, 830

Example 36

2-[4,5-Bis(4-chlorophenyl)-1H-imidazol-2-ylsulfanylmethyl]pyridine (T83)

Starting substances: 3.0 g (9.3 mmol) of Z12; 11.5 g (9.3 mmol) of 2-chloromethyl-pyridine HCl; 460 mg (20 mmol) of Na$^0$
Eluent: ethyl acetate
Yield: 1.8 g IR (KBr): $1/\lambda$ (cm$^{-1}$)=1590, 1500, 1435, 820, 775, 745

Example 37

N$^1$N$^1$-Dimethyl-2-[4,5-bis(4-chlorophenyl)-1H-imidazol-2-ylsulfanyl]-acetamide (T87)

Starting substances: 2.5 g (7.8 mmol) of Z12; 1.0 g (7.8 mmol) of 2-chloro-N,N-di-methylacetamide; 230 mg (10 mmol) of Na$^0$
Work-up: recrystallization from methanol
Yield: 1.7 g IR (KBr): $1/\lambda$ (cm$^{-1}$)=1630, 1500, 1480, 825

Example 38

2-[4,5-Diphenyl-1H-imidazol-2-ylsulfanylmethyl]pyridine (T91)

Starting substances: 3.0 g (12 mmol) of Z10; 2.0 g (12 mmol) of 2-chloromethylpyridine HCl; 598 mg (26 mmol) of Na$^0$
Eluent: ethyl acetate/dichloromethane 1:3
Yield: 2.4 g IR (KBr): $1/\lambda$ (cm$^{-1}$)=3060, 2940, 1600, 1590, 1490, 1435, 765, 700, 750, 670

Example 39

2-[4,5-Bis(4-fluorophenyl)-1H-imidazol-2-ylsulfanylmethyl]pyridine (T97)

Starting substances: 5.0 g (17.3 mmol) of Z13; 2.8 g (17.3 mmol) of 2-chloromethyl-pyridine HCl; 830 mg (36 mmol) of Na$^0$
Eluent: ethyl acetate
Yield: 4.1 g IR (KBr): $1/\lambda$ (cm$^{-1}$)=1580, 1495, 1430, 830, 780, 740

Example 40

2-[4,5-Bis(4-trifluoromethylphenyl)-1H-imidazol-2-ylsulfanylmethyl]-pyridine (T100)

Starting substances: 2.9 g (7.7 mmol) of Z14; 1.5 g (7.7 mmol) of 2-chloromethylpyridine HCl; 414 mg (18 mmol) of Na$^0$
Eluent: ethyl acetate
Yield: 1.82 g IR (KBr): $1/\lambda$ (cm$^{-1}$)=3060, 2940, 1620, 1590, 1510, 1440, 1240, 850, 750, 690

Example 41

2-[4-(4-Chlorophenyl)-5-phenyl-1H-imidazol-2-ylsulfanylmethyl]pyridine (T105)

Starting substances: 2.0 g (6.97 mmol) of Z16; 1.2 g (6.97 mmol) of 2-chloromethyl-pyridine HCl; 350 mg (15.2 mmol) of Na$^0$
Eluent: ethyl acetate
Yield: 734 mg IR (KBr): $1/\lambda$ (cm$^{-1}$)=1590, 1500, 1430, 830, 770, 700, 740 g) Compounds which were obtained by nucleophilic substitution of the 4,5-diaryl-1H-imidazole-2-thiols in the 2-position with the aid of n-butyllithium

Example 42

[4,5-Bis(4-methoxyphenyl)-1H-imidazol-2-yl]-N,N-dimethylcarbamic acid thioester (T1)

1.0 g (3.2 mmol) of the compound Z11 from example 11 was suspended in absolute THF, cooled to −50° C. and 2.5 ml (4 mmol) of BuLi were injected under nitrogen. The mixture was stirred in the cold for 5 min and 0.4 g (3.2 mmol) of N,N-dimethylcarbamoyl chloride, which was dissolved in THF, was then added dropwise. The reaction mixture was stirred overnight at RT. The work-up was carried out by means of column chromatography on silica gel, eluting with ethyl acetate. 740 mg of the compound mentioned in the title were obtained.

IR (KBr): $1/\lambda$ (cm$^{-1}$)=1660, 1615, 1525, 1505, 1460, 1250, 840

Example 43

[4,5-Bis(4-methoxyphenyl)-1H-imidazol-2-yl]-N,N-diethylcarbamic acid thioester (T2)

The synthesis was carried out as described in example 42, except that in the after addition of the BuLi, N,N-diethylcarbamoyl chloride was added. 841 mg of the compound mentioned in the title were obtained.

IR (KBr): $1/\lambda$ (cm$^{-1}$)=2970, 1650, 1610, 1570, 1500, 1455, 1240, 830

In an analogous manner to that described in the example 42, the compounds below were prepared from the starting substances mentioned:

Example 44

[4,5-Bis(4-methoxyphenyl)-1H-imidazol-2-yl]-N,N-diisopropylcarbamic acid thioester (T3)

Starting substances: 2.5 g (8 mmol) of Z11; 1.3 g (8 mmol) of diisopropylcarbamoyl chloride; 6.5 ml (10 mmol) of BuLi
Eluent: ethyl acetate/dichloromethane 1:10
Yield: 840 mg IR (KBr): $1/\lambda$ (cm$^{-1}$)=2830, 1665, 1610, 1500, 1460, 1420, 1245, 830

Example 45

[4,5-Bis(4-methoxyphenyl)-1H-imidazol-2-yl]-morpholine-4-carbamic acid thioester (T4)

Starting substances: 2.5 g (8.1 mmol) of Z11; 1.2 g (8.1 mmol) of morpholine-4-carbamoyl chloride; 6.1 ml (9.8 mmol) of BuLi
Eluent: ethyl acetate
Yield: 2.1 g IR (KBr): $1/\lambda$ (cm$^{-1}$)=2960, 2815, 1650, 1605, 1570, 1500, 1450, 1240, 1210, 830

Example 46

N$^1$,N$^1$-Dimethyl-2-[4,5-bis(4-methoxyphenyl)-1H-imidazol-2-ylsufanyl]-3-oxobutanamide (T7)

Starting substances: 1.0 g (3.2 mmol) of Z11; 10.5 g (3.2 mmol) of 2-chloro-N,N-di-methylacetoacetamide; 3 ml (4.8 mmol) of BuLi
Eluent: ethyl acetate
Yield: 281 mg IR (KBr): $1/\lambda$ (cm$^{-1}$)=2960, 2820, 1750, 1715, 1635, 1610, 1570, 1500, 1460, 1245, 830

Example 47

N$^1$-Phenyl-2-[4,5-bis(4-methoxyphenyl)-1H-imidazol-2-ylsufanyl]acetamide (T9)

Starting substances: 1.0 g (3.2 mmol) of Z11; 0.6 g (3.2 mmol) of N-(2-chloroacetyl)-aniline; 2.1 ml (3.4 mmol) of BuLi
Eluent: ethyl acetate/dichloromethane 1:3
Yield: 687 mg IR (KBr): $1/\lambda$ (cm$^{-1}$)=1670, 1610, 1560, 1500, 1440, 1245, 830, 750, 690

Example 48

N$^1$-(4-Chlorophenyl)-2-[4,5-bis(4-methoxyphenyl)-1H-imidazol-2-yl-sufanyl]acetamide (T10)

Starting substances: 1.0 g (3.2 mmol) of Z11; 0.7 g (3.2 mmol) of Z18; 2.1 ml (3.4 mmol) of BuLi
Eluent: ethyl acetate/dichloromethane 1:3
Yield: 430 mg IR (KBr): $1/\lambda$ (cm$^{-1}$)=1660, 1600, 1500, 1450, 1250, 830

Example 49

3-[4,5-Bis(4-methoxyphenyl)-1H-imidazol-2-ylsufanyl]-1-phenylpropan-1-one (T13)

Starting substances: 660 mg (1.9 mmol) of Z11; 324 mg (1.9 mmol) of β-chloro-propiophenone; 1.4 ml (2.1 mmol) of BuLi
Eluent: ethyl acetate/dichloromethane 1:5
Yield: 100 mg IR (KBr): $1/\lambda$ (cm$^{-1}$)=1680, 1610, 1580, 1510, 1470, 1255, 840, 750, 700

Example 50

N-hu 1-{2-[4,5-Bis(4-methoxyphenyl)-1H-imidazol-2-ylsufanyl]ethyl}-4-chlorobenzenesulfonamide (T18)

Starting substances: 6.76 g (21.6 mmol) of Z11; 5.50 g (21.6 mmol) of Z19; 14.0 ml (22.4 mmol) of BuLi
Eluent: ethyl acetate/dichloromethane 1:10
Yield: 5.6 g IR (KBr): $1/\lambda$ (cm$^{-1}$)=2840, 1610, 1580, 1500, 1460, 1320, 1250, 1160, 835

Example 51

N$^1$-{2-[4,5-Bis(4-methoxyphenyl)-1-methyl-1H-imidazol-2-ylsufanyl]-ethyl}benzamide (T30)

Starting substances: 457 mg (1.4 mmol) of Z15; 257 mg (1.4 mmol) of N-(2-chloro-ethyl)benzamide; 1.0 ml (1.6 mmol) of BuLi
Eluent: ethyl acetate/dichloromethane 1:3
Yield: 350 mg IR (KBr): $1/\lambda$ (cm$^{-1}$)=1655, 1615, 1580, 1500, 1460, 1250, 840, 760, 710

Example 52

N$^1$-{2-[4,5-Bis(4-methoxyphenyl)-1H-imidazol-2-ylsulfanyl]ethyl}acetamide (T49)

Starting substances: 2.5 g (8 mmol) of Z11; 1.0 g (8 mmol) of N-(2-chloroethyl)-acetamide; 5.7 ml (9 mmol) of BuLi
Eluent: ethyl acetate
Yield: 1.7 g IR (KBr): $1/\lambda$ (cm$^{-1}$)=2960, 1630, 1610, 1550, 1500, 1450, 1240, 830

Example 53

[4,5-Bis(4-chlorophenyl)-1H-imidazol-2-yl]-N,N-dimethylcarbamic acid thioester (T81)

Starting substances: 2.5 g (7.8 mmol) of Z12; 0.8 g (7.8 mmol) of N,N-dimethyl-carbamoyl chloride; 5.1 ml (8.2 mmol) of BuLi
Eluent: ethyl acetate
Yield: 2.25 g IR (KBr): $1/\lambda$ (cm$^{-1}$)=1660, 1600, 1500, 1485, 830

Example 54

[4,5-Bis(4-chlorophenyl)-1H-imidazol-2-yl]-N,N-diethylcarbamic acid thioester (T82)

Starting substances: 2.5 g (7.78 mmol) of Z12; 0.93 g (7.78 mmol) of N,N-diethylcarbamoyl chloride; 5.1 ml (8.16 mmol) of BuLi
Eluent: dichloromethane
Yield: 2.2 g IR (KBr): $1/\lambda$ (cm$^{-1}$)=2960, 1670, 1500, 1405, 830

Example 55

N$^1$-{2-[4,5-Bis(4-chlorophenyl)-1H-imidazol-2-ylsufanyl]ethyl}acetamide (T84)

Starting substances: 1.0 g (3.1 mmol) of Z12; 0.4 g (3.1 mmol) of N-(2-chloroethyl)-acetamide; 2.1 ml (3.4 mmol) of BuLi
Eluent: ethyl acetate
Yield: 0.97 g IR (KBr): $1/\lambda$ (cm$^{-1}$)=1635, 1550, 1500, 1410, 830

Example 56

N¹-{2-[4,5-Bis(4-chlorophenyl)-1H-imidazol-2-ylsufanyl]ethyl}benzamide (T85)

Starting substances: 0.8 g (2.5 mmol) of Z12; 0.5 g (2.5 mmol) of N-(2-chloroethyl)-benzamide; 1.7 ml (2.7 mmol) of BuLi Eluent: ethyl acetate/dichloromethane 1:3

Yield: 71 mg IR (KBr): $1/\lambda$ (cm$^{-1}$)=2900, 1630, 1500, 1400, 830

Example 57

N-hu 1-{2-[4,5-Bis(4-chlorophenyl)-1H-imidazol-2-ylsufanyl]ethyl}-4-chloro-benzenesulfonamide (T86)

Starting substances: 500 mg (1.6 mmol) of Z12; 464 mg (1.6 mmol) of Z20; 1.2 ml (1.9 mmol) of BuLi Eluent: ethyl acetate/petroleum ether 1:2

Yield: 167 mg IR (KBr): $1/\lambda$ (cm$^{-1}$)=3290, 3060, 2840, 1580, 1500, 1480, 1320, 1150, 825

Example 58

2-(4,5-Diphenyl)-1H-imidazol-2-yl)-N,N-dimethylcarbamic acid thioester (T89)

Starting substances: 2.0 g (7.95 mmol) of Z10; 0.9 g (7.97 mmol) of N,N-dimethyl-carbamoyl chloride; 5.6 ml (9 mmol) of BuLi Eluent: ethyl acetate Yield: 1.6 g IR (KBr): $1/\lambda$ (cm$^{-1}$)=1660, 1480, 1430, 760, 695

Example 59

2-(4,5-Diphenyl)-1H-imidazol-2-yl)-N,N-diethylcarbamic acid thioester (T90)

Starting substances: 808 mg (3.2 mmol) of Z10; 434 mg (3.2 mmol) of N,N-diethyl-carbamoyl chloride; 2.1 ml (3.4 mmol) of BuLi Eluent: ethyl acetate/petroleum ether 1:1

Yield: 295 mg IR (KBr): $1/\lambda$ (cm$^{-1}$)=1650, 1600, 1570, 1500, 1445, 1245, 760, 695

Example 60

N¹-[2-(4,5-Diphenyl)-1H-imidazol-2-ylsufanyl]ethyl]acetamide (T93)

Starting substances: 1.0 g (4.0 mmol) of Z10; 0.5 g (4.0 mmol) of N-(2-chloroethyl)-acetamide; 2.6 ml (4.2 mmol) of BuLi Eluent: ethyl acetate Yield: 755 mg IR (KBr): $1/\lambda$ (cm$^1$)=1650, 1600, 1570, 1510, 1440, 770, 700

Example 61

N-hu 1-[2-(4,5-Diphenyl)-1H-imidazol-2-ylsufanyl]ethyl]benzamide (T94)

Starting substances: 1.0 g (4.0 mmol) of Z10; 0.7 g (4.0 mmol) of N-(2-chloroethyl)-benzamide; 2.6 ml (4.2 mmol) of BuLi Eluent: ethyl acetate/dichloromethane 1:3

Yield: 700 mg IR (KBr): $1/\lambda$ (cm$^{-1}$)=3070, 2940, 1640, 1600, 1550, 1490, 1450, 770, 700

Example 62

[4,5-Bis(4-fluorophenyl)-1H-imidazol-2-yl]-N,N-dimethylcarbamic acid thioester (T95)

Starting substances: 2.5 g (8.7 mmol) of Z13; 0.9 g (8.7 mmol) of N,N-dimethyl-carbamoyl chloride; 6 ml (9.6 mmol) of BuLi Eluent: ethyl acetate Yield: 1.5 g IR (KBr): $1/\lambda$ (cm$^{-1}$)=1675, 1605, 1500, 835

Example 63

[4,5-Bis(4-fluorophenyl)-1H-imidazol-2-yl]-N,N-diethylcarbamic acid thioester (T96)

Starting substances: 2.5 g (8.67 mmol) of Z13; 1.2 g (8.67 mmol) of N,N-diethyl-carbamoyl chloride; 6.5 ml (10.4 mmol) of BuLi Eluent: ethyl acetate/dichloromethane 1:6

Yield: 2.2 g IR (KBr): $1/\lambda$ (cm$^{-1}$)=1670, 1610, 1590, 1500, 1460, 840

Example 64

N¹-{2-[4,5-Bis(4-fluorophenyl)-1H-imidazol-2-ylsufanyl]ethyl}benzamide (T98)

Starting substances: 1.0 g (3.5 mmol) of Z13; 0.7 g (3.5 mmol) of N-(2-chloroethyl)-benzamide; 2.3 ml (3.7 mmol) of BuLi Eluent: ethyl acetate/dichloromethane 1:1

Yield: 541 mg IR (KBr): $1/\lambda$ (cm$^{-1}$)=1630, 1600, 1545, 1500, 1400, 835

Example 65

[4,5-Bis(4-trifluoromethylphenyl)-1H-imidazol-2-yl]-N,N-diethylcarbamic acid thioester (T99)

Starting substances: 1.0 g (2.57 mmol) of Z14; 0.3 g (2.57 mmol) of N,N-dimethyl-carbamoyl chloride; 1.8 ml (2.88 mmol) of BuLi Eluent: ethyl acetate/dichloromethane 1:3

Yield: 583 mg IR (KBr): $1/\lambda$ (cm$^{-1}$)=2940, 1650, 1610, 1580, 1500, 1450, 1255, 840

Example 66

N¹-{2-[4,5-Bis(4-trifluoromethylphenyl)-1H-imidazol-2-ylsufanyl]ethyl}-acetamide (T101)

Starting substances: 1.0 g (2.6 mmol) of Z14; 0.3 g (2.6 mmol) of N-(2-chloroethyl)-acetamide; 1.7 ml (2.7 mmol) of BuLi

Example 67

N$^1$-{2-[4,5-Bis(4-trifluoromethylphenyl)-1H-imidazol-2-ylsufanyl]ethyl}-benzamide (T102)

Starting substances: 1.0 g (2.6 mmol) of Z14; 0.3 g (2.5 mmol) of N-(2-chloroethyl)-benzamide; 1.7 ml (2.7 mmol) of BuLi Eluent: ethyl acetate/dichloromethane 1:3

Yield: 630 mg IR (KBr): 1/$\lambda$ (cm$^{-1}$)=3060, 2930, 1620, 1575, 1490, 1420, 845, 710

Example 68

[4-(4-Chlorophenyl)-5-phenyl-1H-imidazol-2-yl]-N,N-dimethylcarbamic acid thioester (T103)

Starting substances: 2.0 g (7.0 mmol) of Z16; 0.8 g (7.0 mmol) of N,N-dimethyl-carbamoyl chloride; 5.3 ml (8.4 mmol) of BuLi Eluent: ethyl acetate Yield: 1.45 g IR (KBr): 1/$\lambda$ (cm$^{-1}$)=1650, 1600, 1500, 1480, 830, 765, 695

Example 69

[4-(4-Chlorophenyl)-5-phenyl-1H-imidazol-2-yl]-N,N-diethylcarbamic acid thioester (T104)

Starting substances: 2.0 g (7.0 mmol) of Z16; 1.0 g (7.0 mmol) of N,N-diethylcarbamoyl chloride; 5.3 ml (8.4 mmol) of BuLi Eluent: ethyl acetate/dichloromethane 1:3

Yield: 1.6 g IR (KBr): 1/$\lambda$ (cm$^{-1}$)=1670, 1500, 1485, 830, 770, 700

Example 70

N$^1$-{2-[4-(4-Chlorophenyl)-5-phenyl-1H-imidazol-2-ylsufanyl]ethyl}benzamide (T106)

Starting substances: 1.0 g (3.5 mmol) of Z16; 0.6 g (3.5 mmol) of N-(2-chloroethyl)-benzamide; 2.3 ml (3.7 mmol) of BuLi Eluent: ethyl acetate/dichloromethane 1:3

Yield: 538 mg IR (KBr): 1/$\lambda$ (cm$^{-1}$)=3060, 2920, 1640, 1600, 1540, 1500, 1475, 830, 770, 700

Example 71

[4-(4-Chlorophenyl)-5-(4-methoxyphenyl)-1H-imidazol-2-yl]-N,N-dimethylcarbamic acid thioester (T107)

Starting substances: 2.5 g (7.9 mmol) of Z17; 0.9 g (7.9 mmol) of N,N-dimethyl-carbamoyl chloride; 6.0 ml (9.5 mmol) of BuLi Eluent: ethyl acetate Yield: 1.2 g IR (KBr): 1/$\lambda$ (cm$^{-1}$)=2960, 1650, 1600, 1500, 1480, 1240, 820

Example 72

[4-(4-Chlorophenyl)-5-(4-methoxyphenyl)-1H-imidazol-2-yl]-N N-diethyl-carbamic acid thioester (T108)

Starting substances: 2.5 g (7.9 mmol) of Z17; 0.9 g (7.9 mmol) of N,N-diethyl-carbamoyl chloride; 6.0 ml (9.5 mmol) of BuLi Eluent: ethyl acetate/dichloromethane 1:10

Yield: 1.2 g IR (KBr): 1/$\lambda$ (cm$^{-1}$)=2960, 1640, 1600, 1500, 1480, 1240, 825

Example 73

N$^1$-{2-[4-(4-Chlorophenyl)-5-(4-methoxyphenv)-1H-imidazol-2-yl-sufanyl]ethyl}benzamide (T110)

Starting substances: 0.5 g (1.6 mmol) of Z17; 0.3 g (1.6 mmol) of N-(2-chloroethyl)-benzamide; 1.2 ml (1.9 mmol) of BuLi Eluent: ethyl acetate/dichloromethane 1:3

Yield: 130 mg IR (KBr): 1/$\lambda$ (cm$^{-1}$)=3060, 2940, 1640, 1615, 1560, 1490, 1460, 1250, 835, 740, 710

Example 74

N$^1$-{2-[4-(4-Chlorophenyl)-5-(4-methoxyphenv)-1H-imidazol-2-yl-sufanyl]ethyl}-4-chlorobenzene-sulfonamide (T111)

Starting substances: 0.5 g (1.6 mmol) of Z17; 471 mg (1.6 mmol) of Z20; 1.2 ml (1.9 mmol) of BuLi Eluent: ethyl acetate/petroleum ether 1:2

Yield: 226 mg IR (KBr): 1/$\lambda$ (cm$^{-1}$)=1610, 1565, 1505, 1455, 1310, 1240, 1150, 825 h) Compounds which were obtained by reaction of 4,5-diaryl-1H-imidazol-2-yl-sulfanylalkylamines with carboxylic acid or sulfonic acid halides

Example 75

N$^1$-{2-[4,5-Bis(4-methoxyphenyl)-1H-imidazol-2-ylsulfanyl]propyl}benzamide (T16)

500 mg (1.4 mmol) of the compound Z 21 from Example 21 were suspended in dry THF, cooled to −50° C. and 1.0 ml (1.6 mmol) of BuLi was injected under nitrogen. After stirring for 5 minutes, 190 mg (1.4 mmol) of benzoyl chloride, which were dissolved in dry THF, were added dropwise. The reaction mixture was stirred overnight. The product was purified on a silica gel column, eluting with ethyl acetate. 234 mg of the compound named in the title were obtained.

IR (KBr): 1/$\lambda$ (cm$^{-1}$)=1635, 1610, 1575, 1500, 1465, 1250, 835, 710, 710

In an analogous manner to that described in the example 75, the compounds below were prepared from the starting substances mentioned:

Eluent: ethyl acetate

Yield: 677 mg IR (KBr): 1/$\lambda$ (cm$^{-1}$)=1650, 1610, 1560, 1460, 845

Example 76

N$^1$-{2-[4,5-Bis(4-methoxyphenyl)-1H-imidazol-2-ylsufanyl]ethyl}benzene-sulfonamide (T17)

Starting substances: 500 mg (1.4 mmol) of T15 from Example 28; 250 mg (1.4 mmol) of benzoylsulfonyl chloride; 1.0 ml (1.6 mmol) of BuLi Eluent: ethyl acetate/dichloromethane 1:5

Yield: 200 mg IR(KBr): 1/λ (cm$^{-1}$)=1610, 1500, 1450, 1320, 1250, 1150, 830, 750, 690

Example 77

N-hu 1-{2-[4,5-Bis(4-methoxyphenyl)-1H-imidazol-2-ylsufanyl]ethyl}-4-chlorobenzenesulfonamide (T18)

Starting substances: 500 mg (1.4 mmol) of T15 from Example 28; 300 mg (1.4 mmol) of 4-chlorobenzoylsulfonyl chloride; 1.0 ml (1.6 mmol) of BuLi Eluent: ethyl acetate/dichloromethane 1:10

Yield: 446 mg IR (KBr): 1/λ (cm$^{-1}$)=2840, 1610, 1580, 1500, 1460, 1320, 1250, 1160, 835

Example 78

N$^1$-{2-[4,5-Bis(4-methoxyphenyl)-1H-imidazol-2-ylsufanyl]ethyl}-4-fluorobenzenesulfonamide (T20)

Starting substances: 500 mg (1.4 mmol) of T15 from Example 28; 272 mg (1.4 mmol) of 4-fluorobenzoylsulfonyl chloride; 1.0 ml (1.6 mmol) of BuLi Eluent: ethyl acetate/petroleum ether 1:1

Yield: 347 mg IR (KBr): 1/λ (cm$^{-1}$)=2840, 1610, 1590, 1500, 1460, 1320, 1250, 1160, 830

Example 79

N$^1$-{2-[4,5-Bis(4-methoxyphenyl)-1H-imidazol-2-ylsufanyl]ethyl}-4-nitro-benzenesulfonamide (T21)

Starting substances: 500 mg (1.4 mmol) of T15 from Example 28; 313 mg (1.4 mmol) of 4-nitrobenzoylsulfonyl chloride; 1.0 ml (1.6 mmol) of BuLi Eluent: ethyl acetate/dichloromethane 1:10

Yield: 455 mg IR (KBr): 1/λ (cm$^{-1}$)=2840, 1610, 1525, 1500, 1460, 1440, 1350, 1250, 1160, 835

Example 80

N$^1$-{2-[4,5-Bis(4-methoxyphenyl)-1H-imidazol-2-ylsufanyl]ethyl}-3,5-bis-(trifluoromethyl)benzene-sulfonamide (T22)

Starting substances: 500 mg (1.4 mmol) of T15 from Example 28; 438 mg (1.4 mmol) of 4-bis(trifluoromethyl)benzoylsulfonyl chloride; 1.0 ml (1.6 mmol) of BuLi Eluent: ethyl acetate/petroleum ether 1:2

Yield: 405 mg IR (KBr): 1/λ (cm$^{-1}$)=1600, 1510, 1490, 1455, 1350, 1240, 1155, 825

Example 81

N$^1$-{2-[4,5-Bis(4-methoxyphenyl)-1H-imidazol-2-ylsufanyl]ethyl}-4-methoxybenzenesulfonamide (T23)

Starting substances: 500 mg (1.4 mmol) of T15 from Example 28; 289 mg (1.4 mmol) of 4-methoxybenzoylsulfonyl chloride; 1.0 ml (1.6 mmol) of BuLi Eluent: ethyl acetate/dichloromethane 1:5

Yield: 387 mg IR (KBr): 1/λ (cm$^{-1}$)=1610, 1590, 1500, 1455, 1330, 1240, 1155, 825

Example 82

N$^1$-{2-[4,5-Bis(4-methoxyphenyl)-1H-imidazol-2-ylsufanyl]ethyl}-4-methylbenzenesulfonamide (T24)

Starting substances: 500 mg (1.4 mmol) of T15 from Example 28; 250 mg (1.4 mmol) of p-toluenesulfonyl chloride; 1.0 ml (1.6 mmol) of BuLi Eluent: ethyl acetate/dichloromethane 1:5

Yield: 430 mg IR (KBr): 1/λ (cm$^{-1}$)=1610, 1570, 1500, 1450, 1320, 1240, 1150, 830

Example 83

N$^1$-{2-[4,5-Bis(4-methoxyphenyl)-1H-imidazol-2-ylsufanyl]ethyl}-2,4,6-trimethylbenzenesulfonamide (T25)

Starting substances: 500 mg (1.4 mmol) of T15 from Example 28; 306 mg (1.4 mmol) of mesetylenesulfonyl chloride; 1.0 ml (1.6 mmol) of BuLi Eluent: ethyl acetate/petroleum ether 1:1

Yield: 430 mg IR (KBr): 1/λ (cm$^{-1}$)=1615, 1520, 1505, 1465, 1325, 1250, 1160, 840

Example 84

N$^1$-{2-[4,5-Bis(4-methoxyphenyl)-1H-imidazol-2-ylsufanyl]ethyl}-4-(tert-butyl)benzenesulfonamide (T26)

Starting substances: 500 mg (1.4 mmol) of T15 from Example 28; 326 mg (1.4 mmol) of 4-tert-butylbenzoylsulfonyl chloride; 1.0 ml (1.6 mmol) of BuLi Eluent: ethyl acetate/petroleum ether 1:1

Yield: 368 mg IR (KBr): 1/λ (cm$^{-1}$)=1615, 1525, 1465, 1330, 1255, 1170, 840

Example 85

N$^1$-(4-{2-[4,5-Bis(4-methoxyphenyl)-1H-imidazol-2-ylsufanyl]ethyl-sulfamoyl}phenyl)acetamide (T27)

Starting substances: 500 mg (1.4 mmol) of T15 from Example 28; 327 mg (1.4 mmol) of 4-acetamidobenzenesulfonyl chloride; 1.0 ml (1.6 mmol) of BuLi Eluent: ethyl acetate Yield: 360 mg IR (KBr): 1/λ (cm$^{-1}$)=1680, 1610, 1590, 1500, 1460, 1320, 1250, 1150, 835

Example 86

N¹-{2-[4,5-Bis(4-methoxyphenyl)-1H-imidazol-2-ylsufanyl]ethyl}-4-chlorobenzamide (T32)

Starting substances: 840 mg (2.4 mmol) of T15 from Example 28; 420 mg (2.4 mmol) of 4-chlorobenzoyl chloride; 1.6 ml (2.6 mmol) of BuLi Eluent: ethyl acetate/dichloromethane 2:1

Yield: 636 mg IR (KBr): $1/\lambda$ (cm$^{-1}$)=1630, 1590, 1560, 1500, 1455, 1240, 830

Example 87

N¹-{2-[4,5-Bis(4-methoxyphenyl)-1H-imidazol-2-ylsufanyl]ethyl}-3-chlorobenzamide (T33)

Starting substances: 500 mg (1.4 mmol) of T15 from Example 28; 327 mg (1.4 mmol) of 4-chlorobenzoyl chloride; 1.0 ml (1.6 mmol) of BuLi Eluent: ethyl acetate/dichloromethane 1:3

Yield: 344 mg IR (KBr): $1/\lambda$ (cm$^{-1}$)=2840, 1640, 1615, 1570, 1500, 1465, 1250, 840, 805

Example 88

N¹-{2-[4,5-Bis(4-methoxyphenyl)-1H-imidazol-2-ylsufanyl]ethyl}-2-chlorobenzamide (T34)

Starting substances: 500 mg (1.4 mmol) of T15 from Example 28; 247 mg (1.4 mmol) of 2-chlorobenzoyl chloride; 1.0 ml (1.6 mmol) of BuLi Eluent: ethyl acetate/dichloromethane 1:3

Yield: 300 mg IR (KBr): $1/\lambda$ (cm$^{-1}$)=1645, 1615, 1600, 1500, 1465, 1250, 840, 750

Example 89

N¹-{2-[4,5-Bis(4-methoxyphenyl)-1H-imidazol-2-ylsufanyl]ethyl}-2,4-dichlorobenzamide (T35)

Starting substances: 500 mg (1.4 mmol) of T15 from Example 28; 295 mg (1.4 mmol) of 2,4-dichlorobenzoyl chloride; 1.0 ml (1.6 mmol) of BuLi Eluent: ethyl acetate/dichloromethane 1:3

Yield: 120 mg IR (KBr): $1/\lambda$ (cm$^{-1}$)=2960, 2840, 1640, 1610, 1585, 1500, 1460, 1250, 835

Example 90

N¹-{2-[4,5-Bis(4-methoxyphenyl)-1H-imidazol-2-ylsufanyl]ethyl}-2,6-dichlorobenzamide (T36)

Starting substances: 500 mg (1.4 mmol) of T15 from Example 28; 295 mg (1.4 mmol) of 2,6-dichlorobenzoyl chloride; 1.0 ml (1.6 mmol) of BuLi Eluent: ethyl acetate/dichloromethane 1:6

Yield: 470 mg IR (KBr): $1/\lambda$ (cm$^{-1}$)=2840, 1650, 1615, 1580, 1500, 1460, 1430, 1250, 840, 780

Example 91

N¹-{2-[4,5-Bis(4-methoxyphenyl)-1H-imidazol-2-ylsulfanyl]ethyl}-3,5-dichlorobenzamide (T37)

Starting substances: 500 mg (1.4 mmol) of T15 from Example 28; 293 mg (1.4 mmol) of 3,5-dichlorobenzoyl chloride; 1.0 ml (1.6 mmol) of BuLi Eluent: ethyl acetate/dichloromethane 1:3

Yield: 527 mg IR (KBr): $1/\lambda$ (cm$^{-1}$)=1650, 1620, 1570, 1510, 1470, 1255, 840

Example 92

N¹-{2-[4,5-Bis(4-methoxyphenyl)-1H-imidazol-2-ylsufanyl]ethyl}-4-fluorobenzamide (T38)

Starting substances: 500 mg (1.4 mmol) of T15 from Example 28; 223 mg (1.4 mmol) of 4-fluorobenzoyl chloride; 1.0 ml (1.6 mmol) of BuLi Eluent: ethyl acetate/dichloromethane 1:3

Yield: 95 mg IR (KBr): $1/\lambda$ (cm$^{-1}$)=1630, 1600, 1550, 1500, 1455, 1240, 830

Example 93

N¹-{2-[4,5-Bis(4-methoxyphenyl)-1H-imidazol-2ylsulfanyl]ethyl}-4-cyanobenzamide (T39)

Starting substances: 500 mg (1.4 mmol) of T15 from Example 28; 234 mg (1.4 mmol) of 4-cyanobenzoyl chloride; 1.0 ml (1.6 mmol) of BuLi Eluent: ethyl acetate Yield: 384 mg IR (KBr): $1/\lambda$ (cm$^{-1}$)=1650, 1615, 1560, 1505, 1440, 1250, 840

Example 94

N¹-{2-[4,5-Bis(4-methoxyphenyl)-1H-imidazol-2-ylsufanyl]ethyl}-4-nitro-benzamide (T40)

Starting substances: 500 mg (1.4 mmol) of T15 from Example 28; 262 mg (1.4 mmol) of 4-nitrobenzoyl chloride; 1.0 ml (1.6 mmol) of BuLi Eluent: ethyl acetate/dichloromethane 1:3

Yield: 523 mg IR (KBr): $1/\lambda$ (cm$^{-1}$)=1640, 1600, 1560, 1500, 1440, 1345, 1250, 835

Example 95

N¹-{2-[4,5-Bis(4-methoxyphenyl)-1H-imidazol-2-ylsulfanyl]ethyl}-2-nitro-benzamide (T41)

Starting substances: 500 mg (1.4 mmol) of T15 from Example 28; 262 mg (1.4 mmol) of 2-nitrobenzoyl chloride; 1.0 ml (1.6 mmol) of BuLi Eluent: ethyl acetate/dichloromethane 1:3

Yield: 523 mg IR (KBr): $1/\lambda$ (cm$^{-1}$)=2840, 1645, 1610, 1560, 1500, 1440, 1350, 1250, 840, 730

Example 96

N¹-{2-[4,5-Bis(4-methoxyphenyl)-1H-imidazol-2-ylsufanyl]ethyl}-4-(tri-fluoromethyl)benzamide (T42)

Starting substances: 500 mg (1.4 mmol) of T15 from Example 28; 294 mg (1.4 mmol) of 4-trifluoromethylbenzoyl chloride; 1.0 ml (1.6 mmol) of BuLi Eluent: ethyl acetate/dichloromethane 1:3

Yield: 400 mg IR (KBr): $1/\lambda$ (cm$^{-1}$)=1640, 1610, 1570, 1500, 1460, 1250, 830

Example 97

N¹-{2-[4,5-Bis(4-methoxyphenyl)-1H-imidazol-2-ylsufanyl]ethyl}-3-(tri-fluoromethyl)benzamide (T43)

Starting substances: 500 mg (1.4 mmol) of T15 from Example 28; 294 mg (1.4 mmol) of 3-trifluoromethylbenzoyl chloride; 1.0 ml (1.6 mmol) of BuLi Eluent: ethyl acetate/dichloromethane 1:3

Yield: 400 mg IR (KBr): $1/\lambda$ (cm$^{-1}$)=1640, 1610, 1590, 1500, 1430, 1250, 840, 760

Example 98

N¹-{2-[4,5-Bis(4-methoxyphenyl)-1H-imidazol-2-ylsufanyl]ethyl}-3,5-bis-(trifluoromethyl)benzamide (T44)

Starting substances: 500 mg (1.4 mmol) of T15 from Example 28; 391 mg (1.4 mmol) of 3,5-bis(trifluoromethyl)benzoyl chloride; 1.0 ml (1.6 mmol) of BuLi Eluent: ethyl acetate/dichloromethane 1:3

Yield: 400 mg IR (KBr): $1/\lambda$ (cm$^{-1}$)=1655, 1620, 1580, 1510, 1465, 1250, 840

Example 99

N¹-{2-[4,5-Bis(4-methoxyphenyl)-1H-imidazol-2-ylsufanyl]ethyl}-4-methoxybenzamide (T46)

Starting substances: 500 mg (1.4 mmol) of T15 from Example 28; 240 mg (1.4 mmol) of p-anisoyl chloride; 1.0 ml (1.6 mmol) of BuLi Eluent: ethyl acetate/dichloromethane 1:1

Yield: 384 mg IR (KBr): $1/\lambda$ (cm$^{-1}$)=1620, 1580, 1500, 1460, 1255, 840

Example 100

N¹-{2-[4,5-Bis(4-methoxyphenyl)-1H-imidazol-2-ylsufanyl]ethyl}-3,4,5-trimethoxybenzamide (T46)

Starting substances: 500 mg (1.4 mmol) of T15 from Example 28; 323 mg (1.4 mmol) of 3,4,5-trimethoxybenzoyl chloride; 1.0 ml (1.6 mmol) of BuLi Eluent: ethyl acetate Yield: 200 mg IR (KBr): $1/\lambda$ (cm$^{-1}$)=2930, 2820, 1620, 1605, 1570, 1495, 1450, 1240, 830

Example 101

N¹-{2-[4,5-Bis(4-methoxyphenyl)-1H-imidazol-2-ylsulfanyl]ethyl}4-methylbenzamide (T47)

Starting substances: 500 mg (1.4 mmol) of T15 from Example 28; 218 mg (1.4 mmol) of p-toluoyl chloride; 1.0 ml (1.6 mmol) of BuLi Eluent: ethyl acetate/dichloromethane 1:3

Yield: 357 mg IR (KBr): $1/\lambda$ (cm$^{-1}$)=1615, 1555, 1460, 1250, 830

Example 102

N¹-{2-[4,5-Bis(4-methoxyphenyl)-1H-imidazol-2-ylsulfanyl]ethyl}-4-(tert-butyl)benzamide (T48)

Starting substances: 500 mg (1.4 mmol) of T15 from Example 28; 277 mg (1.4 mmol) of 4-tert-butylbenzoyl chloride; 1.0 ml (1.6 mmol) of BuLi Eluent: ethyl acetate/dichloromethane 1:3

Yield: 390 mg IR (KBr): $1/\lambda$ (cm$^{-1}$)=2860, 1630, 1610, 1585, 1500, 1460, 1250, 835

Example 103

N¹-{2-[4,5-Bis(4-methoxyphenyl)-1H-imidazol-2-ylsufanyl]ethyl}-4-(tert-butyl)benzamide (T50)

Starting substances: 500 mg (1.4 mmol) of T15 from Example 28; 130 mg (1.4 mmol) of propionyl chloride; 1.0 ml (1.6 mmol) of BuLi Eluent: ethyl acetate Yield: 317 mg IR (KBr): $1/\lambda$ (cm$^{-1}$)=1730, 1605, 1510, 1495, 1450, 1240, 825

Example 104

N¹-{2-[4,5-Bis(4-methoxyphenyl)-1H-imidazol-2-ylsufanyl]ethyl}-2-methylpropanamide (T51)

Starting substances: 500 mg (1.4 mmol) of T15 from Example 28; 150 mg (1.4 mmol) of isobutyryl chloride; 1.0 ml (1.6 mmol) of BuLi Eluent: ethyl acetate Yield: 217 mg IR (KBr): $1/\lambda$ (cm$^{-1}$)=2960, 1635, 1605, 1515, 1495, 1455, 1240, 830

Example 105

N¹-{2-[4,5-Bis(4-methoxyphenyl)-1H-imidazol-2-ylsulfanyl]ethyl}-2,2-dimethylpropanamide (T52)

Starting substances: 500 mg (1.4 mmol) of T15 from Example 28; 170 mg (1.4 mmol) of pivaloyl chloride; 1.0 ml (1.6 mmol) of BuLi Eluent: ethyl acetate/dichloromethane 1:3

Yield: 219 mg IR (KBr): $1/\lambda$ (cm$^{-1}$)=2970, 1620, 1580, 1525, 1505, 1465, 1250, 840

The compounds below were prepared in an analogous manner to examples 104 and 105:

Example 106

N$^1$-{2-[4,5-Bis(4-methoxyphenyl)-1H-imidazol-2-ylsulfanyl]ethyl}furan-2-carboxamide (T53)

Example 107

N$^1$-{2-[4,5-Bis(4-methoxyphenyl)-1H-imidazol-2-ylsulfanyl]ethyl}thiophene-2-carboxamide (T54)

Example 108

N$^1$-{2-[4,5-Bis(4-methoxyphenyl)-1H-imidazol-2-ylsulfanyl]ethyl}-1-naphthamide (T55)

Example 109

N$^1$-{2-[4,5-Bis(4-methoxyphenyl)-1H-imidazol-2-ylsulfanyl]ethyl}-2-naphthamide (T56)

Example 110

N$^1$-{2-[4,5-Bis(4-methoxyphenyl)-1H-imidazol-2-ylsulfanyl]ethyl}-N',N'-dimethylurea (T57)

Example 111

N$^1$-{2-[4,5-Bis(4-methoxyphenyl)-1H-imidazol-2-ylsulfanyl]ethyl}-N',N'-diethylurea (T58)

Example 112

N$^1$-{2-[4,5-Bis(4-methoxyphenyl)-1H-imidazol-2-ylsulfanyl]ethyl}-2-phenylacetamide (T59)

Example 113

N$^1$-{2-[4,5-Bis(4-methoxyphenyl)-1H-imidazol-2-ylsulfanyl]ethyl}-3-phenylpropanamide (T60)

Example 114

N$^1$-{2-[4,5-Bis(4-methoxyphenyl)-1H-imidazol-2-ylsulfanyl]ethyl}-3-phenylprop-2-enamide (T61)

Example 115

N$^1$-{2-[4,5-Bis(4-methoxyphenyl)-1H-imidazol-2-ylsulfanyl]ethyl}-2,2-diphenylacetamide (T62)

Example 116

N$^1$-{2-[4,5-Bis(4-methoxyphenyl)-1H-imidazol-2-ylsulfanyl]ethyl}-methanesulfonamide (T63)

Example 117

N$^1$-{2-[4,5-Bis(4-methoxyphenyl)-1H-imidazol-2-ylsulfanyl]ethyl}-ethanesulfonamide (T64)

Example 118

N$^1$-{2-[4,5-Bis(4-methoxyphenyl)-1H-imidazol-2-ylsulfanyl]ethyl}-propane-2-sulfonamide (T65)

Example 119

N$^1$-{2-[4,5-Bis(4-methoxyphenyl)-1H-imidazol-2-ylsulfanyl]ethyl}-phenylmethanesulfonamide (T66)

Example 120

N$^1$-{2-[4,5-Bis(4-methoxyphenyl)-1H-imidazol-2-ylsulfanyl]ethyl}-naphthalene-1-sulfonamide (T67)

Example 121

N$^1$-{2-[4,5-Bis(4-methoxyphenyl)-1H-imidazol-2-ylsulfanyl]ethyl}-naphthalene-2-sulfonamide (T68)

i) Synthesis of the ethyl 2-(4,5-diaryl-1H-imidazolyl) acetates

Example 122

Ethyl 2-[4,5-bis(4-methoxyphenyl)-2-(2-pyridylmethylsulfanyl)-1H-imidazol-1-yl]acetate (Z23)

1.3 g (3.3 mmol) of the compound T69 from Example 30 were dissolved in absolute THF and 120 mg (5 mmol) of NaH were added in small portions with stirring. The reaction mixture was stirred at RT for 10 min. 0.5 g (3.3 mmol) of ethyl bromoacetate, dissolved in dry DMF, was then added dropwise. The reaction mixture was then stirred at RT for 2 h. For the work-up, the DMF was evaporated and the residue by means of column chromatography on silica gel, eluting with ethyl acetate. 1.37 g of the compound mentioned in the title were obtained.

The compounds below were prepared from the starting substances mentioned in an analogous manner to that described in example 122:

Example 123

Ethyl 2-[4,5-bis(4-methoxyphenyl)-2-(3-pyridylmethylsulfanyl)-1H-imidazol-1-yl]acetate (Z24)

Starting substances: 500 mg (1.2 mmol) of T70 from Example 31; 270 mg (1.6 mmol) of ethyl bromoacetate; 72 mg (3 mmol) of NaH
Yield: 587 mg

Example 124

Ethyl 2-[4,5-bis(4-methoxyphenyl)-2-(4-pyridylmethylsulfanyl)-1H-imidazol-1-yl]acetate (Z25)

Starting substances: 500 mg (1.2 mmol) of T71 from Example 32; 270 mg (1.6 mmol) of ethyl bromoacetate; 72 mg (3 mmol) of NaH
Yield: 584 mg

Example 125

Ethyl 2-[4,5-bis(4-methoxyphenyl)-2-(2-quinolylmethylsulfanyl)-1H-imidazol-1-yl]acetate (Z26)

Starting substances: 400 mg (0.9 mmol) of T72 from Example 33; 150 mg (0.9 mmol) of ethyl bromoacetate; 30 mg (1.2 mmol) of NaH
Yield: 423 mg

Example 126

Ethyl 2-[4,5-diphenyl-2-(2-pyridylmethylsulfanyl)-1H-imidazol-1-yl]-acetate (Z27)

Starting substances: 1.2 g (3.5 mmol) of T91 from Example 38; 0.4 g (3.5 mmol) of ethyl bromoacetate; 101 mg (4.2 mmol) of NaH
Yield: 1.0 g

Example 127

Ethyl 2-[4-(4-chlorophenyl)-5-(4-methoxyphenyl)-2-(2-pyridylmethyl-sulfanyl)-1H-imidazol-1-yl]acetate (Z28)

Starting substances: 0.85 g (2.1 mmol) of Z22 from Example 22; 0.35 g (2.1 mmol) of ethyl bromoacetate; 0.60 g (2.5 mmol) of NaH
Yield: 788 mg k) Synthesis of the carboxylic acids by ester hydrolysis

Example 128

2-[4,5-Bis(4-methoxyphenyl)-2-(2-pyridylmethylsulfanyl)-1H-imidazol-1-yl]acetic acid (T75)

1.37 g (2.8 mmol) of the compound Z23 from Example 23 were dissolved in ethanol, treated with 5 ml (10 mmol) of 2 N NaOH and refluxed for 2 h. After cooling, the ethanol was stripped off, the residue was treated with water and washed a number of times with dichloromethane. The aqueous phase was acidified to a pH of 6–7 using 10% strength H3PO4 and again extracted by shaking with dichloromethane. The organic phase was dried using $Na_2SO_4$, evaporated and the residue was recrystallized from ethanol. 865 mg of the compound mentioned in the title were obtained.

IR (KBr): $1/\lambda$ $(cm^{-1})$=3400, 1720, 1600, 1510, 1430, 1240, 830, 790, 740

The compounds below were prepared from the starting substances mentioned in an analogous manner to that described in example 128:

Example 129

2-[4,5-Bis(4-methoxyphenyl)-2-(3-pyridylmethylsulfanyl)-1H-imidazol-1-yl]-acetic acid (T76)

Starting substances: 587 mg (1.2 mmol) of Z24 from Example 123; 5 ml (10 mmol) of 2 N NaOH
Yield: 445 mg IR (KBr): $1/\lambda$ $(cm^{-1})$=3450, 2965, 1710, 1600, 1560, 1500, 1410, 1235, 825, 775, 700

Example 130

2-[4,5-Bis(4-methoxyphenyl)-2-(4-pyridylmethylsulfanyl)-1H-imidazol-1-yl]-acetic acid (T77)

Starting substances: 584 mg (1.2 mmol) of Z25 from Example 124; 5 ml (10 mmol) of 2 N NaOH
Yield: 308 mg IR (KBr): $1/\lambda$ $(cm^{-1})$=3450, 2960, 1710, 1600, 1575, 1485, 1410, 1230, 830, 740, 680

Example 131

2-[4,5-Bis(4-methoxyphenyl)-2-(2-quinolylmethylsulfanyl)-1H-imidazol-1-yl]acetic acid (T78)

Starting substances: 423 mg (0.8 mmol) of Z26 from Example 125; 2 ml (4 mmol) of 2 N NaOH
Yield: 305 mg IR (KBr): $1/\lambda$ $(cm^{-1})$=3450, 1720, 1610, 1500, 1420, 1250, 835, 780, 760

Example 132

2-[4,5-Diphenyl-2-(2-pyridylmethylsulfanyl)-1H-imidazol-1-yl]-acetic acid (T92)

Starting substances: 1.0 g (2.3 mmol) of Z27 from Example 126; 7.5 ml (15 mmol) of 2 N NaOH
Yield: 3444 mg IR (KBr): $1/\lambda$ $(cm^{-1})$=3440, 3050, 1720, 1600, 1570, 1500, 1430, 1235, 770, 700, 750, 675

Example 133

2-[4-(4-Chlorophenyl)-5-(4-methoxyphenyl)-2-(2-pyridylmethylsulfanyl) -1H-imidazol-1-yl]acetic acid (Z109)

Starting substances: 788 mg (1.6 mmol) of Z28 from Example 127; 5 ml (10 mmol) of 2 N NaOH
Yield: 242 mg IR(KBr): $1/\lambda$ $(cm^{-1})$=3400, 1715, 1615, 1570, 1510, 1430, 1250, 830, 740, 695 l) Oxidation of thio ethers to sulfones

Example 134

2-[4,5-Bis(4-methoxyphenyl)-1H-imidazol-2-ylsulfonylmethyl]pyridine (T74)

0.2 g (0.5 mmol) of the compound T69 from Example 30 was dissolved in 30 ml of THF/methanol (1:1) and cooled to 0C. 2.3 g (3.7 mmol) of Oxone® (potassium monopersulfate triple salt=$2KHSO_5 \times KHSO_4 \times K_2SO_4$) dissolved in 30 ml of water were then added dropwise. The reaction mixture was stirred overnight. The Oxone® was then filtered off, the organic solvents were stripped off and the aqueous phase was extracted by shaking with ethyl acetate and dichloromethane. The combined organic phases were dried using $Na_2SO_4$ and evaporated. The residue was recrystallized from ethy acetate (alternatively, $CH_2Cl_2$/n-hexane can also be used). 140 mg of the compound mentioned in the title were obtained.

IR(KBr): $1/\lambda$ $(cm^{-1})$=1610, 1520, 1500, 1430, 1330, 1245, 1140, 830, 770, 705

Example 135

Ethyl 2-[4,5-bis(4-methoxyphenyl)-1H-imidazol-2-ylsulfonyl]acetate (T80)

1.0 g (2.5 mmol) of the compound T79 from Example 35 was reacted with 6.1 g (10 mmol) of Oxone® as described in Example 134. 0.9 g of the compound mentioned in the title was obtained.

IR (KBr): $1/$, $(cm^{-1})$=2940, 1740, 1610, 1570, 1500, 1450, 1335, 1250, 1140, 830 m) Alkylation using methyl iodide and NaH

Example 136

2-[4,5-Bis(4-methoxyphenyl)-1-methyl-1H-imidazol-2-ylsulfanyl]-1-(di-methylamino)propan-1-one (T8)

500 mg (1.26 mmol) of the compound T6 from Example 24 were dissolved in DMF.

48 mg (2.0 mmol) of NaH were then added in portions. The mixture was stirred for 10 min and then 358 mg (2.52 mmol) of methyl iodide were added dropwise. The reaction was carried out for 2 h at RT. For the inactivation of the excess NaH, the reaction mixture was then treated with 10 ml of methanol. After evolution of gas had ended, the solvents were stripped off and the residue was purified on a silica gel column using ethyl acetate.

IR (KBr): $1/\lambda$ (cm$^{-1}$)=2940, 1640, 1620, 1620, 1585, 1500, 1455, 1255, 845

The compounds below were prepared analogously to the process described in example 136:

Example 137

$N^1$-{2-[4,5-Bis(4-methoxyphenyl)-1-methyl-1H-imidazol-2-ylsufanyl]-ethyl}-N-1-methyl-4-chlorobenzenesulfonamide (T19)

Starting substances: 400 mg (0.8 mmol) of T18 from Example 50; 284 mg (2.0 mmol) of methyl iodide; 96 mg (4.0 mmol) of NaH Yield: 30 mg IR (KBr): $1/\lambda$ (cm$^{-1}$)=1620, 1590, 1500, 1465, 1350, 1255, 1170, 840

Example 138

$N^1$-{2-[4,5-Bis(4-methoxyphenyl)-1-methyl-1H-imidazol-2-ylsulfanyl]-ethyl}-$N^1$-1-methylbenzamide-4-chlorobenzenesulfonamide (T31)

Starting substances: 340 mg (0.7 mmol) of T28 from Example 29; 213 mg (1.5 mmol) of methyl iodide; 96 mg (4.0 mmol) of NaH Yield: 234 mg IR (KBr): $1/\lambda$ (cm$^{-1}$)=2940, 2820, 1625, 1570, 1490, 1450, 1240, 830, 770, 710

Example 139

2-[4,5-Bis(4-chlorophenyl)-1-methyl-1H-imidazol-2-ylsufanyl]-1-(di-methylamino)propan-1-one (T88)

Starting substances: 500 mg (1.23 mmol) of T87 from Example 37; 350 mg (2.46 mmol) of methyl iodide; 48 mg (2.0 mmol) of NaH Yield: 410 mg IR (KBr): $1/\lambda$ (cm$^{-1}$)=2920, 1640, 1490, 1470, 830 n) Synthesis of $N^1$-{2-[4,5-bis(4-methoxyphenyl)-1H-imidazol-2-ylsulfanyl]ethyl}-$N^1$-1-methylbenzamide

Example 140

$N^1$-{2-[4,5-Bis(4-methoxyphenyl)-1H-imidazol-2ylsulfanyl]ethyl}-$N^1$-1-methylbenzamide (T29)

2.0 g (6.4 mmol) of the compound Z11 from Example 11 were suspended in dry THF and cooled to −50° C. 4.2 ml (6.7 mmol) of n-butyllithium were then injected under nitrogen. After stirring at the low temperature for 5 min, 0.9 g (6.4 mmol) of 1-bromo-2-chloroethane was added dropwise. The cooling bath was removed and the reaction mixture was stirred at RT for 3 h. The mixture was then again cooled to −50° C. and 0.9 g (6.4 mmol) of N-methylbenzamide was added. A further 4.2 ml (6.7 mmol) of n-butyllithium were injected and the reaction mixture was stirred at RT overnight. The product was chromatographed on a silica gel column, eluting with ethyl acetate/petroleum ether (3:1). 200 mg of the compound mentioned in the title were obtained.

Ir (KBr): $1/\lambda$ (cm$^{-1}$)=1600, 1570, 1510, 1450, 1240, 830

The invention claimed is:

1. A compound of the formula I

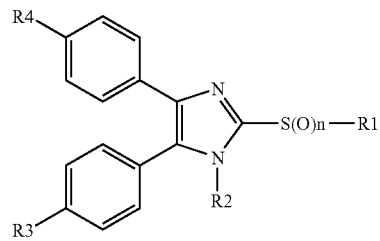

in which $R^1$ is selected from:
a) CONR$^5$R$^6$, in which R$^5$ and R$^6$ independently of one another are H or C$_1$-C$_6$-alkyl;
b) A-CONR$^5$R$^6$, in which A is C$_1$-C$_6$-alkylene which is optionally substituted by C$_1$-C$_3$-alkyl-CO, and R$^5$ and R$^6$ independently of one another are H, C$_1$-C$_6$-alkyl or phenyl which is optionally substituted by one or 2 halogen atoms with the proviso that R$^5$ and R$^6$ are both H;
c) C$_1$-C$_6$-alkylene-R$^7$, where R$^7$ is NR$^5$R$^6$, and R$^5$ and R$^6$ independently of one another are H or C$_1$-C$_6$-alkyl;
d) C$_1$-C$_6$-alkylene-CO—R$^9$, where R$^9$ is phenyl which is substituted by halogen, or C$_2$-C$_6$-alkylene-CO—R$^9$, where R$^9$ is phenyl which is optionally substituted by halogen;
e) C$_1$-C$_6$-alkylene-NR$^{10}$—CO—R$^{11}$, or
f) C$_1$-C$_6$-alkylene-NR$^{10}$—SO$^2$—R$^{12}$, $R^{10}$ is H or C$_1$-C$_6$-alkyl, $R^{11}$ is
naphthyl, or
CH=CH-phenyl;

$R^{12}$ is
phenyl which optionally has 1, 2 or 3 substituents which independently of one another are selected from halogen, NO$_2$, CF$_3$, OC$_1$-C$_6$-alkyl, C$_1$-C$_6$-alkyl, NH$_2$ and NHCOC$_1$-C$_3$-alkyl,
C$_1$-C$_6$-alkyl which is optionally substituted by one or two phenyl groups, or
naphthyl, $R^2$ is H, C$_1$-C$_6$-alkyl or (CH$_2$)$_o$COOH, $R^3$ and $R^4$, which can be identical or different, are H, OH, OC$_1$-C$_6$-alkyl, halogen or C$_1$-C$_6$-alkyl which is substituted by 1, 2 or 3 halogen atoms, where at least one of the radicals R$^3$ and R$^4$ is OH or OC$_1$-C$_6$-alkyl, n is 0, 1 or 2 and o is 0, 1, 2, 3 or 4, and the optical isomers and physiologically tolerable salts thereof.

2. A compound as claimed in claim 1, where $R^1$ is selected from:
  a) $CONR^5R^6$, in which $R^5$ and $R^6$ independently of one another are H or $C_1$-$C_6$-alkyl;
  b) A-$CONR^5R^6$, in which A is $C_1$-$C_6$-alkylene which is optionally substituted by $C_1$-$C_3$-alkyl-CO, and $R^5$ and $R^6$ independently of one another are H, $C_1$-$C_6$-alkyl or phenyl which is optionally substituted by one or 2 halogen atoms, with the proviso that $R^5$ and $R^6$ are both H;
  c) $C_1$-$C_6$-alkylene-CO—$R^9$, where $R^9$ is phenyl which is substituted by halogen, or $C_2$-$C_6$-alkylene-CO—$R^9$, where $R^9$ is phenyl which is optionally substituted by halogen;
  d) $C_1$-$C_6$-alkylene-$NR^{10}$—CO—$R^{11}$;
  e) $C_1$-$C_6$-alkylene-$NR^{10}$—$SO^2$—$R^{12}$,
  $R^{11}$ is naphthyl, or CH=CH-phenyl,
  and $R^2$, $R^3$, $R^4$, $R^{10}$ and $R^{12}$ have the meaning as indicated in claim 1.

3. A compound as claimed in claim 1, where both radicals $R^3$ and $R^4$ are a $C_1$-$C_6$-alkoxy group.

4. A compound as claimed in claim 1, where $R^1$ is A-$CONR^5R^6$ and A, $R^5$ and $R^6$ have the meanings indicated in claim 1.

5. A compound as claimed in claim 1, where $R^1$ is $C_1$-$C_6$-alkylene-CO—$R^9$, in which $R^9$ is phenyl which is substituted by halogen.

6. A compound as claimed in claim 1, where $R^1$ is $C_1$-$C_6$-alkylene-$R^7$, in which $R^7$ is $NR^5R^6$, and $R^5$ and $R^6$ have the meanings indicated in claim 1.

7. A compound of the formula I

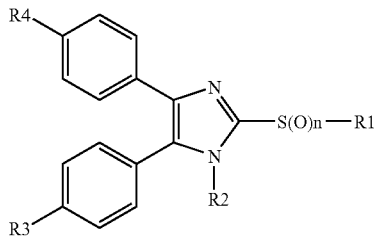

in which
$R^1$ is selected from:
  a) $CONR^5R^6$, in which $R^5$ and $R^6$ independently of one another are H or $C_1$-$C_6$-alkyl,
  b) $C_1$-$C_6$-alkylene-$NR^{10}$—CO—$R^{11}$, in which $R^{11}$ is naphthyl, or
  c) $C_1$-$C_6$-alkylene-$NR^{10}$—$SO^2$—$R^{12}$;
$R^{10}$ is H or $C_1$-$C_6$-alkyl;
$R^{12}$ is
  phenyl which optionally has 1, 2 or 3 substituents which independently of one another are selected from halogen, $NO_2$, $CF_3$, $OC_1$-$C_6$-alkyl, $C_1$-C6-alkyl, $NH_2$ and $NHCOC_1$-$C_3$-alkyl,
  $C_1$-$C_6$-alkyl which is optionally substituted by one or two phenyl groups, or
  naphthyl;
$R^2$ is H, $C_1$-$C_6$-alkyl or $(CH_2)_oCOOH$;
$R^3$ and $R^4$, which can be identical or different are H, OH, $OC_1$-$C_6$-alkyl, halogen or $C_1$-$C_6$-alkyl which is substituted by 1, 2 or 3 halogen atoms, where at least one of the radicals $R^3$ and $R^4$ is OH or $OC_1$-$C_6$-alkyl;
n is 0, 1 or 2; and
o is 0, 1, 2, 3 or 4;

and the optical isomers and physiologically tolerable salts thereof.

8. A compound as claimed in claim 7, where $R^{12}$ is naphthyl or phenyl which has 1, 2 or 3 substituents, which independently of one another are selected from halogen, $NO_2$, $CF_3$, $OC_1$-$C_6$-alkyl, $C_1$-$C_6$-alkyl, $NH_2$ and $NHCOC_1$-$C_3$-alkyl.

9. A compound as claimed in claim 7, where $R^{12}$ is $C_1$-$C_6$-alkyl which is optionally substituted by one or two phenyl groups.

10. A compound as claimed in claim 1, where $R^1$ is $C_1$-$C_6$-alkylene-$NR^{10}$—CO—$R^{11}$, in which $R^{10}$ is H or $C_1$-$C_4$-alkyl and $R^{11}$ is —CH=CH-phenyl.

11. A compound as claimed in claim 10, where $R^1$ is $C_1$-, $C_2$- or $C_3$-alkylene-$NR^{10}$—CO—$R^{11}$, in which $R^{10}$ and $R^{11}$ have the meanings indicated in claim 10.

12. A compound as claimed in claim 1, wherein $R^1$ is $C_2$-$C_6$-alkylene-CO—$R^9$, in which $R^9$ is phenyl optionally substituted by halogen.

13. A compound as claimed in claim 1, wherein A is $C_2$-$C_6$ alkylene which is optionally substituted by $C_1$-$C_3$-alkyl-CO.

14. A compound as claimed in claim 1, wherein n is 1 or 2.

15. A cosmetic composition comprising:
one or more cosmetically acceptable additives; and
at least one compound of the formula I

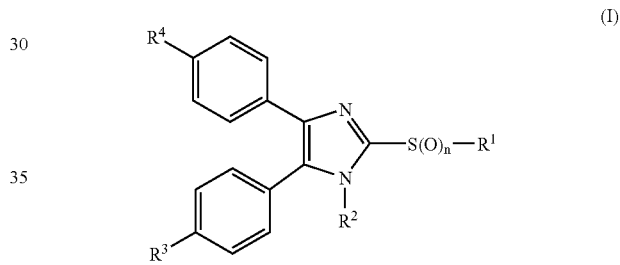

in which
$R^1$ is selected from:
  a) $CONR^5R^6$, in which $R^5$ and $R^6$ independently of one another are H or $C_1$-$C_6$-alkyl;
  b) A-$CONR^5R^6$, in which A is $C_1$-$C_6$-alkylene which is optionally substituted by $C_1$-$C_3$-alkyl-CO, and $R^5$ and $R^6$ independently of one another are H, $C_1$-$C_6$-alkyl or phenyl which is optionally substituted by one or 2 halogen atoms;
  c) $C_1$-$C_6$-alkylene-$R^7$, where $R^7$ is $NR^5R^6$ or is $COOR^8$, wherein $R^5$ and $R^6$ independently of one another are H or $C_1$-$C_6$-alkyl and $R^8$ is H or $C_1$-$C_6$-alkyl;
  d) $C_1$-$C_6$-alkylene-CO—$R^9$, where $R^9$ is phenyl which is optionally substituted by halogen;
  e) $C_1$-$C_6$-alkylene-$NR^{10}$—CO—$R^{11}$; or
  f) $C_1$-$C_6$-alkylene-$NR^{10}$—$SO^2$—$R^{12}$;
$R^{10}$ is H or $C_1$-$C_6$-alkyl;
$R^{11}$ is
  phenyl which is optionally substituted by 1, 2 or 3 substituents, which independently of one another are selected from halogen, CN, $NO_2$, $CF_3$, $OC_1$-C6-alkyl and $C_1$-$C_6$-alkyl,
  naphthyl,
  $C_1$-$C_6$-alkyl which is optionally substituted by 1 or 2 phenyl groups,
  $C_2$-$C_6$-alkenyl,
  CH=CH-phenyl, or NR$^5$R$^6$, where R$^5$ and R$^6$ independently of one another are H or C$_1$-C$_6$-alkyl;

R$^{12}$ is phenyl which optionally has 1, 2 or 3 substituents which independently of one another are selected from halogen, NO$_2$, CF$_3$, OC$_1$-C$_6$-alkyl, C$_1$-C$_6$-alkyl, NH$_2$ and NHCOC$_1$-C$_3$-alkyl, C$_1$-C$_6$-alkyl which is optionally substituted by one or two phenyl groups, or naphthyl;

R$^2$ is H, C$_1$-C$_6$-alkyl or (CH$_2$)$_o$COOH;

R$^3$ and R$^4$, which can be identical or different, are H, OH, OC$_1$-C$_6$-alkyl, halogen or C$_1$-C$_6$-alkyl which is substituted by 1, 2 or 3 halogen atoms, where at least one of the radicals R$^3$ and R$^4$ is OH or OC$_1$-C$_6$-alkyl;

n is 0, 1 or 2; and o is 0, 1, 2, 3 or 4;

and the optical isomers and physiologically tolerable salts thereof.

16. A cosmetic composition as claimed in claim 15, wherein R$^7$ is NR$^5$R$^6$, and R$^5$ and R$^6$ are as defined in claim 15.

17. A cosmetic or pharmaceutical composition comprising at least one compound of the formula I

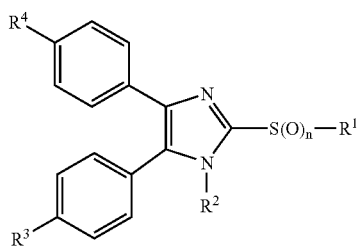

(I)

in which

R$^1$ is selected from:

a) CONR$^5$R$^6$, in which R$^5$ and R$^6$ independently of one another are H or C$_1$-C$_6$-alkyl;

b) A-CONR$^5$R$^6$, in which A is C$_1$-C$_6$-alkylene which is optionally substituted by C$_1$-C$_3$-alkyl-CO, and R$^5$ and R$^6$ independently of one another are H, C$_1$-C$_6$-alkyl or phenyl which is optionally substituted by one or 2 halogen atoms;

c) C$_1$-C$_6$-alkylene-R$^7$, where R$^7$ is NR$^5$R$^6$, and R$^5$ and R$^6$ independently of one another are H or C$_1$-C$_6$-alkyl;

d) C$_1$-C$_6$-alkylene-CO—R$^9$, where R$^9$ is phenyl which is optionally substituted by halogen;

e) C$_1$-C$_6$-alkylene-NR$^{10}$—CO—R$^{11}$; or f) C$_1$-C$_6$-alkylene-NR$^{10}$—SO$^2$—R$^{12}$;

R$^{10}$ is H or C$_1$-C$_6$-alkyl;

R$^{11}$ is naphthyl, or

CH=CH-phenyl

R$^{12}$ is phenyl which optionally has 1, 2 or 3 substituents which independently of one another arc selected from halogen, NO$_2$, CF$_3$, OC$_1$-C$_6$-alkyl, C$_1$-C$_6$-alkyl, NH$_2$ and NHCOC$_1$-C$_3$-alkyl, C$_1$-C$_6$-alkyl which is optionally substituted by one or two phenyl groups, or naphthyl;

R$^2$ is H, C$_1$-C$_6$-alkyl or (CH$_2$)$_o$COOH;

R$^3$ and R$^4$, which can be identical or different, are H, OH, OC$_1$-C$_6$-alkyl, halogen or C$_1$-C$_6$-alkyl which is substituted by 1, 2 or 3 halogen atoms, where at least one of the radicals R$^3$ and R$^4$ is OH or OC$_1$-C$_6$-alkyl;

n is 0, 1 or 2; and o is 0, 1, 2, 3 or 4;

and the optical isomers and physiologically tolerable salts thereof.

18. A method for treating inflammation, comprising topically applying a pharmaceutical composition comprising at least one compound as claimed in claim 1.

19. A method for treating a disease that is connected with an immune system disorder, comprising administering a pharmaceutical composition comprising at least one compound as claimed in claim 1, wherein said disease is selected from the group consisting of premature labor, colon carcinoma, Alzheimer's disease, rheumatoid arthritis, gout, septic shock, osteoporosis, neuropathic pain, alopecia, psoriasis, acute pancreatitis, rejection reactions in allogenic transplants, allergically caused pneumonia, arteriosclerosis, multiple sclerosis, cachexia, inflammatory bowel disease, adenomatous polyposis, inhibition of angiogenesis in connection with oncoses, contact eczema, and erythema.

20. A procedure for the treatment of diseases which are connected with a disorder of the immune system, where an amount of a compound as claimed in claim 1 having an immunomodulating or cyclooxygenase-inhibiting action is administered to a person who needs treatment of this type, and wherein said disease is selected from the group consisting of premature labor, colon carcinoma, Alzheimer's disease, rheumatoid arthritis, gout, septic shock, osteoporosis, neuropathic pain, alopecia, psoriasis, acute pancreatitis, rejection reactions in allogenic transplants, allergically caused pneumonia, arteriosclerosis, multiple sclerosis, cachexia, inflammatory bowel disease, adenomatous polyposis, inhibition of angiogenesis in connection with oncoses, contact eczema, and crythema.

* * * * *

UNITED STATES PATENT AND TRADEMARK OFFICE
CERTIFICATE OF CORRECTION

PATENT NO. : 7,223,781 B2
APPLICATION NO. : 10/672613
DATED : May 29, 2007
INVENTOR(S) : Dannhardt et al.

Page 1 of 1

It is certified that error appears in the above-identified patent and that said Letters Patent is hereby corrected as shown below:

Column 50;

Line 4: "CH=CH-phenyl" should read --CH=CH-phenyl;--

Line 50: "crythema" should read --erythema--

Signed and Sealed this

Thirteenth Day of November, 2007

JON W. DUDAS
*Director of the United States Patent and Trademark Office*